US010099015B2

(12) United States Patent
Bayer et al.

(10) Patent No.: US 10,099,015 B2
(45) Date of Patent: Oct. 16, 2018

(54) DRIVE MECHANISM FOR A DRUG DELIVERY DEVICE

(71) Applicant: SANOFI, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Michael Pfoser, Kohlscheid (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 177 days.

(21) Appl. No.: 14/783,160

(22) PCT Filed: Apr. 8, 2014

(86) PCT No.: PCT/EP2014/056987
§ 371 (c)(1),
(2) Date: Oct. 8, 2015

(87) PCT Pub. No.: WO2014/166907
PCT Pub. Date: Oct. 16, 2014

(65) Prior Publication Data
US 2016/0045668 A1 Feb. 18, 2016

(30) Foreign Application Priority Data
Apr. 10, 2013 (EP) .................... 13163084

(51) Int. Cl.
*A61M 5/315* (2006.01)
*A61M 5/24* (2006.01)
(52) U.S. Cl.
CPC .............. *A61M 5/315* (2013.01); *A61M 5/24* (2013.01); *A61M 5/31511* (2013.01);
(Continued)

(58) Field of Classification Search
CPC .............. A61M 5/315; A61M 5/31511; A61M 5/31541; A61M 5/31543; A61M 5/31553;
(Continued)

(56) References Cited

U.S. PATENT DOCUMENTS 5,505,704 A * 4/1996 Pawelka ................. A61M 5/19
604/191
5,509,905 A 4/1996 Michel
(Continued)

FOREIGN PATENT DOCUMENTS

JP 2013/506447 2/2013
WO WO 1998/056436 12/1998
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Andrew Gilbert
*Assistant Examiner* — Dung Ulsh
(74) *Attorney, Agent, or Firm* — Fish & Richardson P.C.

(57) ABSTRACT

The present invention relates to a drive mechanism for a drug delivery device for dispensing of a dose of a medicament, and to a respective drug delivery device, wherein the drive mechanism comprises: —an elongated housing (30) extending in an axial direction (1, 2), —a piston rod (80) to operably engage with a piston (16) of a cartridge (14) to displace the piston (16) in axial distal direction (1), —a drive sleeve (60) extending in axial direction (1, 2) and being rotatably supported in the housing (30), —a dose setting member (40) rotatably supported on a side wall portion (31) of the housing (30) and being rotatable with respect to an axis (41) extending in radial direction (r), —wherein the
(Continued)

drive sleeve (60) is operably releasable from the piston rod (80) and rotatably engageable with the dose setting member (40) for setting of the dose.

19 Claims, 13 Drawing Sheets

(52) U.S. Cl.
CPC .... *A61M 5/31543* (2013.01); *A61M 5/31553* (2013.01); *A61M 5/31585* (2013.01); *A61M 5/3153* (2013.01); *A61M 5/31501* (2013.01); *A61M 5/31525* (2013.01); *A61M 5/31533* (2013.01); *A61M 5/31541* (2013.01); *A61M 5/31545* (2013.01); *A61M 5/31563* (2013.01); *A61M 5/31565* (2013.01); *A61M 2205/581* (2013.01); *A61M 2205/582* (2013.01)

(58) Field of Classification Search
CPC .......... A61M 5/31585; A61M 5/31525; A61M 5/31533; A61M 5/31545; A61M 5/31565; A61M 5/3153; A61M 5/31501; A61M 5/31535; A61M 5/3155; A61M 5/31563; A61M 2005/31518; A61M 2005/3152; A61M 5/31528; A61M 5/31558; A61M 5/31575

See application file for complete search history.

(56) References Cited

U.S. PATENT DOCUMENTS

| | | | |
|---|---|---|---|
| 5,697,916 A * | 12/1997 | Schraga | A61M 5/1782 604/155 |
| 5,921,966 A * | 7/1999 | Bendek | A61M 5/24 604/207 |
| 6,045,537 A * | 4/2000 | Klitmose | A61M 5/24 604/224 |
| 6,074,372 A * | 6/2000 | Hansen | A61M 5/31525 604/211 |
| 6,364,860 B1 * | 4/2002 | Steck | A61M 5/31553 604/207 |
| 6,582,404 B1 * | 6/2003 | Klitgaard | A61M 5/31525 604/181 |
| 6,663,602 B2 * | 12/2003 | Moller | A61M 5/24 222/390 |
| 8,361,036 B2 * | 1/2013 | Moller | A61M 5/31511 604/211 |
| 8,475,414 B2 * | 7/2013 | Boyd | A61M 5/31555 604/218 |
| 8,652,100 B1 * | 2/2014 | Cowe | A61M 5/2033 604/117 |
| 8,876,766 B2 * | 11/2014 | Holmqvist | A61M 5/2033 604/135 |
| 9,095,657 B2 * | 8/2015 | Holmqvist | A61M 5/20 |
| 9,180,244 B2 * | 11/2015 | Anderson | A61M 5/14248 |
| 9,446,201 B2 * | 9/2016 | Holmqvist | A61M 5/31525 |
| 2001/0014791 A1 * | 8/2001 | Hansen | A61M 5/31525 604/211 |
| 2002/0004651 A1 * | 1/2002 | Ljunggreen | A61M 5/31501 604/218 |
| 2002/0007154 A1 * | 1/2002 | Hansen | A61M 5/20 604/207 |
| 2002/0052578 A1 * | 5/2002 | Moller | A61M 5/24 604/208 |
| 2004/0054326 A1 * | 3/2004 | Hommann | A61M 5/31553 604/131 |
| 2004/0064104 A1 * | 4/2004 | Miller | A61M 5/31525 604/207 |
| 2004/0068236 A1 * | 4/2004 | Moller | A61M 5/31525 604/208 |
| 2004/0210199 A1 * | 10/2004 | Atterbury | A61M 5/31566 604/224 |
| 2006/0069355 A1 * | 3/2006 | Judson | A61M 5/31511 604/211 |
| 2006/0153693 A1 * | 7/2006 | Fiechter | A61M 5/31553 417/63 |
| 2006/0276753 A1 * | 12/2006 | Kronestedt | A61M 5/20 604/186 |
| 2007/0060894 A1 * | 3/2007 | Dai | A61M 5/19 604/207 |
| 2007/0233015 A1 * | 10/2007 | Saiki | A61M 5/31551 604/207 |
| 2007/0244436 A1 * | 10/2007 | Saiki | A61M 5/31511 604/131 |
| 2008/0183139 A1 * | 7/2008 | Burren | A61M 5/31553 604/211 |
| 2009/0043255 A1 * | 2/2009 | Taufig | A61M 5/315 604/111 |
| 2009/0062748 A1 * | 3/2009 | Moller | A61M 5/31511 604/211 |
| 2009/0082727 A1 * | 3/2009 | Moeller | A61M 5/14224 604/132 |
| 2009/0275900 A1 * | 11/2009 | Hetherington | A61M 5/31511 604/208 |
| 2010/0137792 A1 * | 6/2010 | Boyd | A61M 5/31555 604/68 |
| 2010/0152671 A1 * | 6/2010 | Raab | A61M 5/31551 604/207 |
| 2010/0292651 A1 * | 11/2010 | Yodfat | A61M 5/1413 604/189 |
| 2010/0305501 A1 * | 12/2010 | Ratjen | A61M 5/2448 604/82 |
| 2010/0324492 A1 * | 12/2010 | Peruzzo | A61M 5/31511 604/198 |
| 2010/0324528 A1 * | 12/2010 | Plumptre | A61M 5/24 604/506 |
| 2010/0331791 A1 * | 12/2010 | Plumptre | A61M 5/31551 604/207 |
| 2011/0004166 A1 * | 1/2011 | Wittmann | A61M 5/20 604/207 |
| 2011/0054412 A1 * | 3/2011 | Eich | A61M 5/20 604/207 |
| 2011/0068124 A1 | 3/2011 | Reynolds et al. | |
| 2011/0092905 A1 * | 4/2011 | Cowe | A61M 5/20 604/135 |
| 2011/0098657 A1 * | 4/2011 | Jennings | A61J 1/2096 604/198 |
| 2011/0245780 A1 * | 10/2011 | Helmer | A61M 5/31515 604/211 |
| 2011/0313365 A1 * | 12/2011 | Wieselblad | A61M 5/31525 604/207 |
| 2012/0004620 A1 * | 1/2012 | Spool | A61M 5/24 604/211 |
| 2012/0004639 A1 * | 1/2012 | Schoonmaker | A61M 5/204 604/506 |
| 2012/0010575 A1 * | 1/2012 | Jones | A61M 5/31555 604/211 |
| 2012/0055632 A1 * | 3/2012 | de la Llera | H01R 13/20 156/345.34 |
| 2012/0095413 A1 * | 4/2012 | Nzike | A61M 5/3148 604/211 |
| 2012/0172815 A1 * | 7/2012 | Holmqvist | A61M 5/20 604/208 |
| 2012/0253287 A1 * | 10/2012 | Giambattista | A61M 5/31553 604/189 |
| 2012/0283647 A1 * | 11/2012 | Cronenberg | A61M 5/31535 604/207 |
| 2012/0283658 A1 * | 11/2012 | Plumptre | A61M 5/24 604/211 |
| 2012/0289908 A1 * | 11/2012 | Kouyoumjian | A61M 5/31543 604/211 |
| 2012/0296276 A1 * | 11/2012 | Nicholls | A61M 5/31501 604/110 |
| 2013/0041322 A1 * | 2/2013 | Holmqvist | A61M 5/31525 604/189 |
| 2013/0096495 A1 * | 4/2013 | Holmqvist | A61M 5/2033 604/89 |

(56) References Cited

U.S. PATENT DOCUMENTS

| | | | |
|---|---|---|---|
| 2013/0204195 A1* | 8/2013 | Ekman | A61M 5/2033 604/197 |
| 2013/0211336 A1* | 8/2013 | Holmqvist | A61M 5/24 604/189 |
| 2013/0218095 A1* | 8/2013 | Butler | A61M 5/31541 604/207 |
| 2013/0245558 A1* | 9/2013 | Holmqvist | A61M 5/31525 604/189 |
| 2013/0296778 A1* | 11/2013 | Damgaard-Soerensen | A61M 5/2448 604/82 |
| 2014/0171879 A1* | 6/2014 | Butler | A61M 5/31525 604/218 |
| 2014/0200519 A1* | 7/2014 | Kjeldsen | A61M 5/3129 604/207 |
| 2014/0257195 A1* | 9/2014 | Kjeldsen | A61M 5/31541 604/207 |
| 2014/0350480 A1* | 11/2014 | Keitel | A61M 5/31551 604/210 |
| 2015/0065963 A1* | 3/2015 | Kjeldsen | A61M 5/31541 604/207 |
| 2015/0190577 A1* | 7/2015 | Shaanan | G08B 21/02 604/66 |
| 2016/0045668 A1* | 2/2016 | Mayer | A61M 5/24 604/207 |

FOREIGN PATENT DOCUMENTS

| | | |
|---|---|---|
| WO | WO 2001/003008 | 11/2001 |
| WO | WO 2004/007003 | 1/2004 |
| WO | WO 2007/104697 | 9/2007 |
| WO | WO 2011/039208 | 4/2011 |
| WO | WO 2011/136718 | 11/2011 |

OTHER PUBLICATIONS

International Preliminary Report on Patentability in International Application No. PCT/EP2014/056987, dated Oct. 10, 2015, 8 pages.
International Search Report and Written Opinion in International Application No. PCT/EP2014/056987, dated Nov. 11, 2014, 11 pages.

* cited by examiner

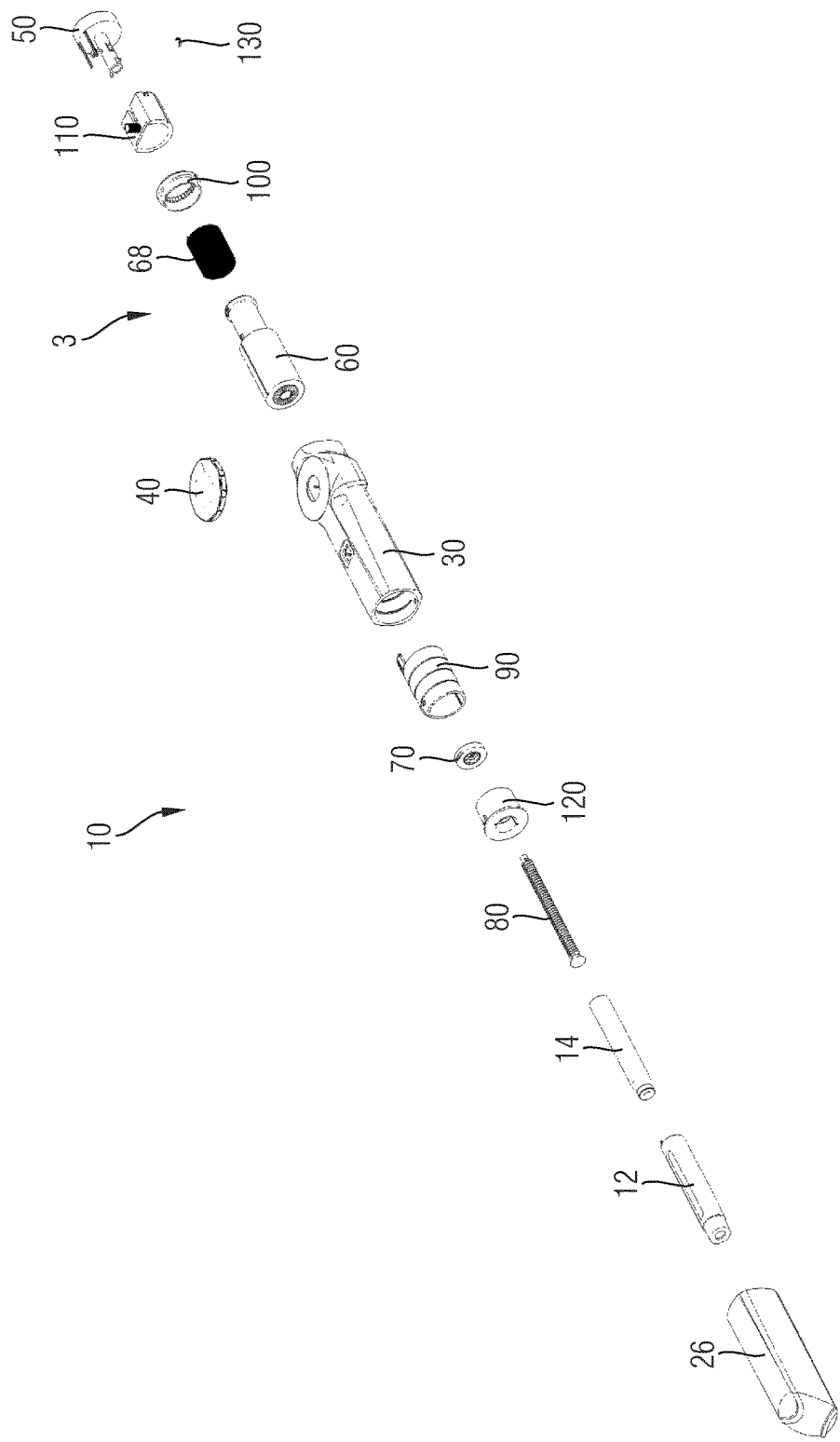

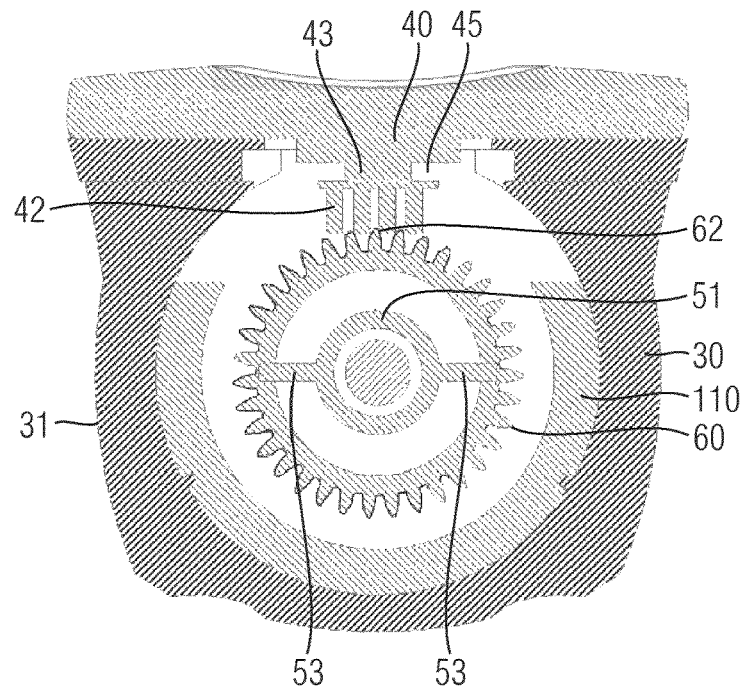
Fig. 4 A-A
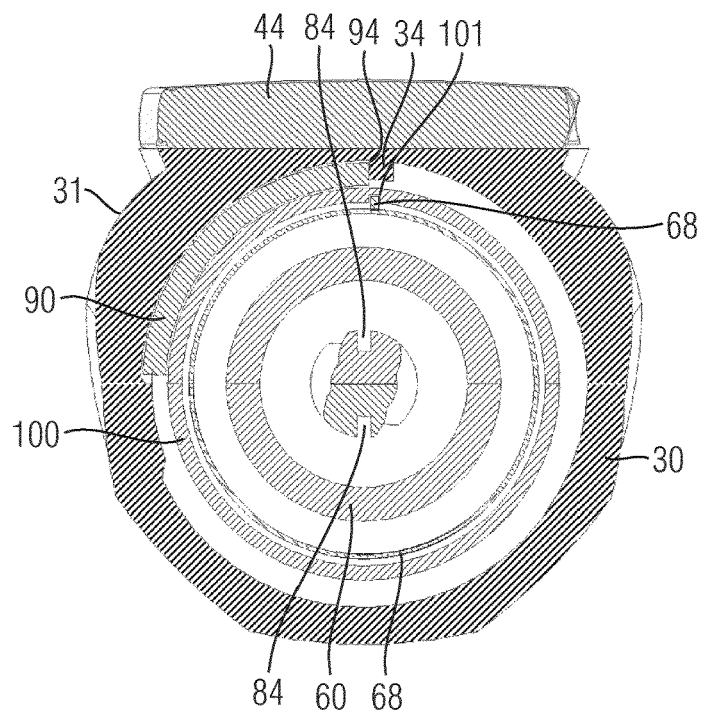
Fig. 5 B-B

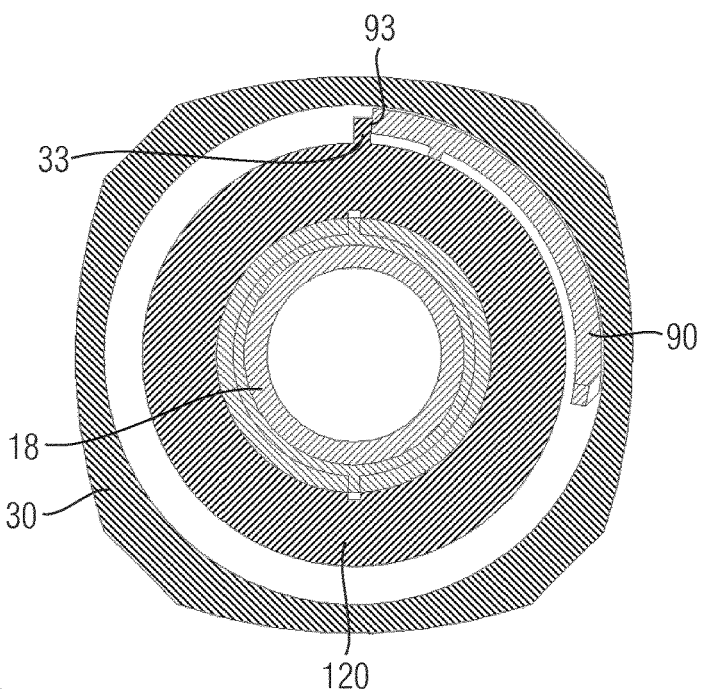
Fig. 6 C-C
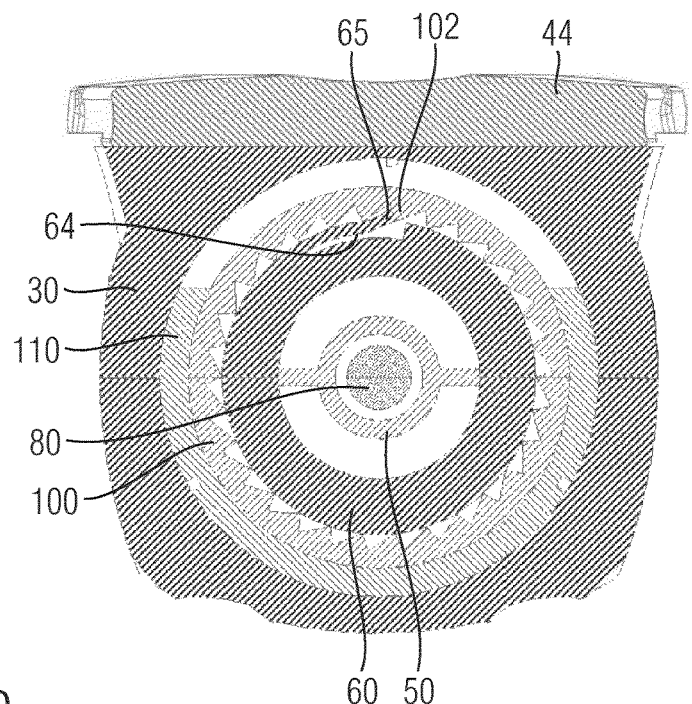
Fig. 7 D-D

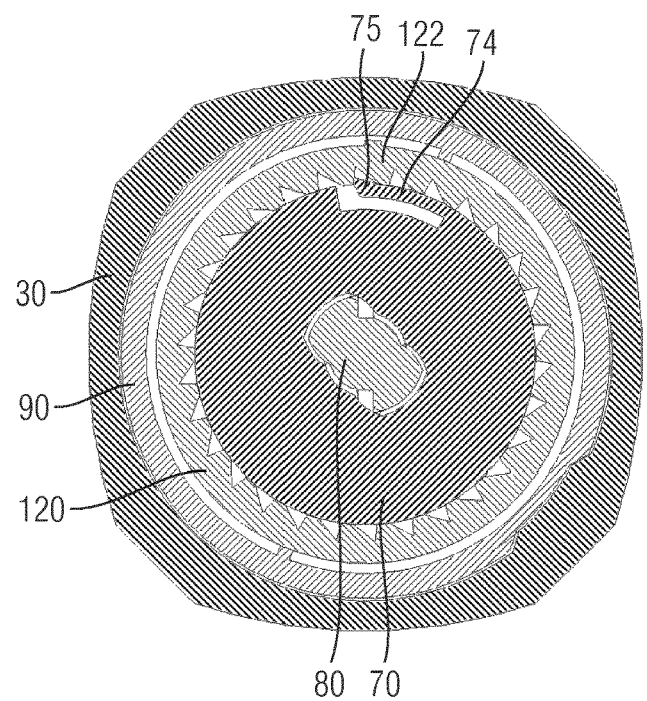
Fig. 8 E-E
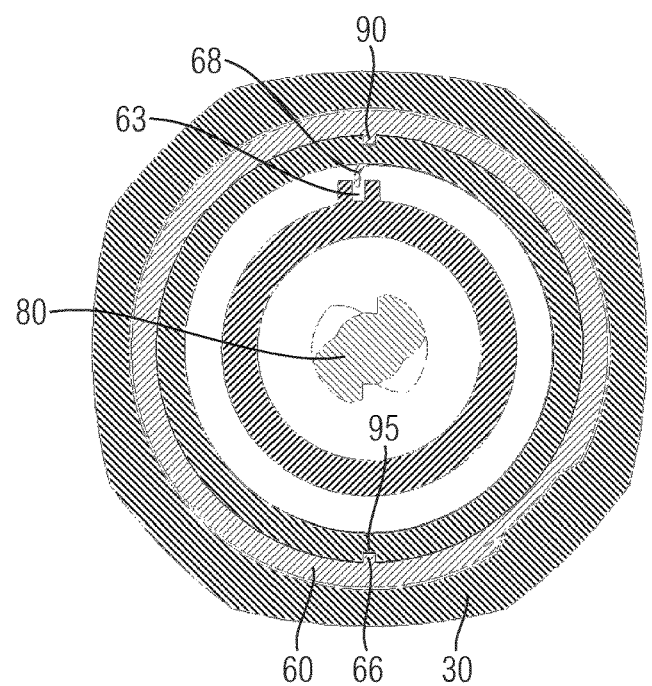
Fig. 9 F-F

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/056987, filed on Apr. 8, 2014, which claims priority to European Patent Application No. 13163084.0, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected.

There already exist some drug delivery devices with end-of-content mechanisms or last dose mechanisms.

Document WO 2004/007003 A1 for instance discloses an end-of-content arrangement for preventing a dose setting member of an injection device to be set to a dose larger than the medicament remaining in the injection device. There is described a dose setting and injecting mechanism featuring an arm flexibly hinged to a coupling ring. Said arm is equipped with a cam engaging a spiral-shaped track provided on a driver. When a dose setting member and the coupling ring is rotated in a clockwise direction during the setting of a dose, the cam on the arm is moved along the track in an outward direction whereas the cam, during injection, due to the concomitant rotation of the coupling ring and the driver remains in its position in the track obtained during the dose setting.

The length of the spiral track is synchronised with the content in the cartridge such that the cam is guided out through the track opening when the cartridge is almost empty.

With many of these known approaches the last dose limiting mechanism is located rather remote from an actuation member, such like a dose dial member, by way of which the user may interact with the drive mechanism, e.g. for setting and/or dispensing of a dose. For limiting or delimiting a dose setting procedure, the angular momentum or driving force exerted by a user of the device has to be transferred from the actuation member almost through the entire drive mechanism and the plurality of its mutually interacting components until the last dose limiting mechanism is eventually activated and blocks a further dose incrementing movement of the drive mechanism and of its various components.

Since the mechanically interacting components of a drive mechanism are always subject to inevitable mechanical tolerances, a respective tolerance chain extending between the actuation member, e.g. a dose dial, and the last dose limiting mechanism may be fairly long. In effect, once a last dose limiting mechanism is activated and actually inhibits a dose incrementing displacement of e.g. a drive sleeve relative to a housing or relative to a piston rod, the locking or blocking of e.g. the drive sleeve has to propagate and to be transferred or returned to the dose dial member. Also here, due to the tolerance chain at least a minimal displacement, e.g. a rotation of the dose dial member may still be possible even though a dose incrementing displacement of the drive mechanism is effectively blocked.

Apart from such a last dose limiting mechanism it may be also required to provide a single dose limiting mechanism by way of which the maximum size of a dose to be set and dispensed can be limited to a predefined maximum.

It is therefore an object of the present invention to avoid disadvantages of known drug delivery devices and to provide a drive mechanism for a drug delivery device allowing for an intuitive operation, both for setting and for dispensing of a dose.

It is another object of the present invention to provide a drive mechanism for a drug delivery device for setting and dispensing of a dose of a medicament typically provided in a cartridge, wherein the drive mechanism is equipped with a single dose limiting mechanism and with a last dose limiting mechanism.

It is a further object to provide a drug delivery device comprising such a drive mechanism and comprising a cartridge sealed with a piston to become operably engaged with a piston rod of such drive mechanism.

In a first aspect a drive mechanism for a drug delivery device is provided for dispensing of a dose of a medicament. The drive mechanism comprises an elongated housing extending in an axial direction. Preferably, the housing is of substantially tubular or cylindrical shape that allows gripping and operating of the drive mechanism or of the entire drug delivery device by one hand of a user.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge that corresponds to the axial displacement of the piston. The piston typically seals the cartridge in axial proximal direction. The piston rod serves to displace the piston of the cartridge in an axial distal direction. The piston rod is therefore operable to apply distally directed thrust or pressure to the piston of the cartridge for displacing the same in distal direction for a predetermined distance that corresponds to a respective amount of the medicament to be dispensed.

The drive mechanism further comprises at least one drive sleeve extending in axial direction and being rotatably supported in the housing. The drive sleeve is operably releasable from the piston rod for setting of a dose. Hence, during a dose setting procedure, the piston rod remains substantially stationary with respect to the housing while the drive sleeve, operably disconnected and released from the piston rod, is rotatable relative to the housing and hence relative to the piston rod.

Additionally, the drive mechanism comprises a dose setting member rotatably supported on a side wall portion of the housing and being rotatable with respect to an axis extending in radial direction with respect to the axially elongated housing. Hence, the dose setting member, typically comprising a rotatable dose dial or an actuation wheel is located on a lateral side wall portion and may be operable, hence rotatable for setting of a dose. The dose setting member and the drive sleeve are operably engageable at least for setting of a dose. Mutual engagement of the dose setting member and the drive sleeve is such that a rotation of the dose setting member with respect to the radially extending axis is transferred to a respective rotation of the drive sleeve, which is rotatably supported in the housing along the axial direction.

Arrangement of a dose setting member on a side wall portion of the housing provides an intuitive handling of the drive mechanism and the drug delivery device. Arrangement of a dose setting member on or in a side wall portion of the housing allows to spatially separate the dose setting member from a dose injection member, which is typically arranged at a proximal end of the housing and which is designed to be operated by a user's thumb. Moreover, by arranging a dose setting member on or in a side wall portion of the housing, the overall size of the dose setting member can be increased compared to an arrangement, where the dose setting member is located at a proximal end of the elongated housing.

According to another embodiment, the drive sleeve is operably engageable with the piston rod and is operably releasable from the dose setting member for dispensing of the dose.

For dispensing of the set dose, the drive sleeve is operably engageable with the piston rod. In a respective dose dispensing mode, piston rod and drive sleeve are operably engaged for that the drive sleeve may exert a driving force or driving momentum to the piston rod for driving the same in distal direction to displace the piston of the cartridge accordingly.

Typically, the drive sleeve is either operably engageable with the piston rod or with the dose setting member, depending on whether the drive mechanism is in dose dispensing or in dose setting mode. When in dose setting mode, the drive sleeve is operably engaged, hence rotatably engaged with the dose setting member while it is actually operably released from the piston rod. This way, a dose of variable size can be set by means of the dose setting member leading to a respective rotational and/or longitudinal displacement of the drive sleeve.

Typically, displacement of the drive sleeve during a dose setting procedure is accompanied by tensioning of a spring element, which is operable to return and to displace the drive sleeve in the opposite direction during a subsequent dose dispensing procedure. During such a dose dispensing procedure or in dose dispensing mode, the piston rod and the drive sleeve are operably engaged, preferably in such a way, that a rotation of the drive sleeve is transferred to a distally directed axial displacement of the piston rod for driving the piston further into the cartridge. Since the drive sleeve is operably released from the dose setting member during dose dispensing the dose setting member remains substantially stationary, e.g. for not irritating or confusing a user of the device.

According to a further embodiment, the drive sleeve is displaceable in axial direction between a proximal dose setting position and a distal dose injecting position for selectively and alternately engaging and disengaging with the piston rod and with the dose setting member. Typically, the drive sleeve is either engaged with the piston rod or with the dose setting member. In particular, when in distal dose injecting position, the drive sleeve is operably engaged with the piston rod and is operably released from the dose setting member. In the proximal dose setting position, the drive sleeve is directly operably, hence rotatably engaged with the dose setting member while it is operably released from the piston rod.

Since the drive sleeve is alternately engageable with either the piston rod or with the dose setting member, the drive sleeve serves as a kind of a clutch arrangement allowing the drive mechanism to switch between a dose setting mode and a dose dispensing mode. Moreover, switching between these two modes may be predominantly governed by the axial displacement of the drive sleeve alone between its distal dose injecting position and its proximal dose setting position. This way, a rather simple, robust and reliable clutch arrangement can be provided.

Typically, the drive sleeve encloses the circumference of the piston rod at least in an axial section. The drive sleeve is open towards the distal direction and receives or accommodates a proximal portion of the piston rod, at least in an initial device configuration. The piston rod and the surrounding drive sleeve are typically arranged concentrically. Hence, the piston rod is located in the radial centre of the drive sleeve and is co-aligned with the drive sleeve in axial direction. While the drive sleeve is rotatably supported in the housing it may only experience a limited axial displacement, e.g. for switching between the dose setting mode and the dose dispensing mode of the drive mechanism. In contrast to that, the piston rod advances in distal direction with every consecutive dose dispensing procedure. With repeated dose dispensing procedures the piston rod may therefore protrude more and more in axial direction from the drive sleeve.

According to another embodiment, the drive mechanism further comprises a dose injection member at a proximal end of the housing. The dose injection member is displaceable in axial direction between a proximal dose setting position and a distal dose injecting position. The dose injection member further distally abuts with the drive sleeve for displacing the drive sleeve into the dose injecting position. Preferably, the dose injection member extends into the housing of the drive mechanism with an axially extending shaft portion. A distal end of the shaft portion or a radially widened or radially outwardly extending abutment piece thereof abuts in distal direction and against a proximal end face of the drive sleeve.

This way, exerting a distally directed pressure to the dose injection member leads to a respective distally directed displacement of the dose injection member relative to the housing, thereby urging or pushing the drive sleeve in distal direction accordingly. In effect, the drive sleeve can be displaced from the proximal dose setting position into the distal dose injecting position by means of the dose injection member. This way, switching between a dose dispensing mode and a dose setting mode of the drive mechanism is basically operable by a simple depressing of the dose injection member in distal direction.

Additionally and according to another embodiment, the dose injection member is rotatably fixed to the housing and comprises a locking or catch member to engage with the dose setting member when reaching the dose injecting position. The locking member may comprise an arm or L-shaped beam extending radially outwardly from an axially extending shaft portion of the dose injection member. Since the dose injection member is rotatably fixed to the housing it may not rotate relative to the longitudinal axis.

Hence, the dose injection member may be only allowed to slidably move in distal and proximal direction between the above mentioned proximal dose setting position and the distal dose injection position. Since the locking member radially outwardly extends from the shaft portion of the dose injection member it may engage or may interlock with the dose setting member in such a way, that further rotation of the dose setting member relative to the housing is effectively blocked when the dose injection member is in its distal dose injecting position. Said mutual engagement of the locking member of the dose injection member with the dose setting member therefore effectively hinders the dose setting member to move or to rotate any further when the drive mechanism is in dose dispensing mode.

Hence, the locking member is therefore operable to allow a rotation of the dose setting member only when the drive mechanism is in its dose setting mode. Typically, the locking member comprises a toothed free end to engage with a gear wheel of the dose setting member in the dose injecting position, thereby inhibiting any further displacement or rotation of the dose setting member.

In another preferred embodiment, the drive sleeve is displaceable in distal direction relative to the housing against the action of a spring element axially acting between the drive sleeve and the housing. By means of the at least one spring element, the drive sleeve may return into its proximal dose setting position as soon as a distally directed thrust acting on the drive sleeve drops below a predefined threshold. In the event that a user prematurely releases the dose injection member, the drive sleeve will immediately return into its dose setting position under the effect of the tensioned spring element.

Since the drive sleeve is in axial abutment with the dose injection member also the injection member will return into its initial dose setting position as soon as a user's thumb no longer depresses the dose injection member in distal direction. The spring element may be arranged axially between a radially inwardly extending support of the housing and a respective support located on the outside of the drive sleeve.

Furthermore, the at least one spring element may be integrally formed with either the housing or with the drive sleeve. This way, a separate step of assembling the spring element between the drive sleeve and the housing can be omitted. Preferably, the spring element is located at a distal end face of the drive sleeve. It may axially extend and project against an insert fixedly arranged in the housing of the drive mechanism.

Alternatively, the spring element may also engage with the housing directly. Moreover, the insert, which is typically adapted to axially guide and to receive the piston rod, may also be integrally formed with the housing.

According to a further embodiment, the dose setting member comprises a gear wheel located inside the housing to engage with a crown wheel of the drive sleeve when in dose setting position. The crown wheel of the drive sleeve is typically located on a proximal end face of the drive sleeve while the gear wheel of the dose setting member is oriented parallel to an actuation wheel of the dose setting member extending outside the housing. The gear wheel of the dose setting member is preferably rotatable with respect to the radially extending axis of the dose setting member.

The gear wheel may be integrally formed with and may thus be integrated into the dose setting member. Since the gear wheel directly engages with a crown wheel of the drive sleeve, which may also be integrally formed with a drive sleeve, a direct mutual engagement of dose setting member and drive sleeve can be attained. This way, a tolerance chain and a mechanical path between various mutually interacting components of the drive mechanism can be kept rather short, thereby providing a direct feedback to a user and allowing for a precise setting and adjusting of a dose.

Since the gear wheel of the dose setting member directly engages with the crown wheel of the drive sleeve, the angular momentum of the dose setting member rotating around a radial axis can be directly transferred into a respective angular momentum of the drive sleeve rotating around a longitudinal axis extending in axial direction.

Hence, by the direct and mutual interaction of the dose setting member's gear wheel with the crown wheel of the drive sleeve, the direction of angular momentum inside the drive mechanism can be deflected, e.g. about 90°, from the radial direction into the axial direction.

In a further embodiment a support member is provided fixedly attached to the housing and having a radially outwardly extending socket portion to support a hollow shaft of the dose setting member. The support member is typically to be arranged into a proximal receptacle of the housing. Preferably, the support member and the housing member may be mutually fixed by means of mutually engaging grooves or latch elements, by way of which the support member can be fixed relative to the housing in axial as well as in circumferential or tangential direction.

The support member serves as a rotative support for the dose setting member. For this purpose, the support member comprises a radially outwardly extending socket portion to engage with a hollow shaft of the dose setting member. Here, the socket portion of the support member may not protrude radially from the housing. Hence, the radially outwardly extending socket portion of the support member lies completely inside the tubular housing and may flush with a through opening of the housing to be covered by the dose setting member.

Alternative to the above mentioned mutual engagement of support member and dose setting member it is also conceivable, that the support member comprises a radially inwardly extending receptacle adapted to receive a correspondingly shaped shaft of the dose setting member. Typically, the dose setting member is rotatable relative to the support member along the axis of rotation extending in radial direction. It is preferably the radially outwardly extending socket portion that forms said axis or bearing for the dose setting member. Preferably, support member and dose setting member are not threadedly engaged so that the dose setting member does not experience a radial offset when dialed, e.g. in a dose incrementing or dose decrementing direction.

According to another preferred aspect, the support member further comprises an axially extending receptacle at a proximal end to slidably receive the dose injection member. The support member, in particular its receptacle, and the dose injection member may be rotatably fixed, e.g. by means of mutually corresponding and radially extending grooves and protrusions. The dose injection member may be splined to the support member. The support member may for instance comprise at least one axially extending groove to receive a correspondingly shaped and radially extending protrusion so that the dose injection member can be slidably supported in axial direction but is rotatably fixed relative to the support member.

Preferably, rotatable fixing of support member and the dose injection member can be achieved by means of the radially outwardly extending locking or catch member of the dose injection member slidably disposed in axial direction in a correspondingly shaped axially extending groove of the support member. Preferably, said groove can be opened in proximal direction, thereby allowing to insert the dose injection member in distal direction into the support member upon assembly of the drive mechanism.

This way, the locking member provides a double function. On the one hand it serves to rotatably interlock with the dose setting member and on the other hand it inhibits a rotation of the dose injection member itself around the longitudinal axis relative to the support member. Moreover, the support member and the dose injection member are axially fixed, e.g. by means of a snap-in feature provided on the outer circumference of the axially extending shaft portion of the dose injection member. Accordingly, the support member typically comprises a recessed portion to receive, e.g. a radially outwardly extending snap- or latch element of the dose injection member.

According to a further preferred embodiment, a last dose limiting member is arranged between the socket portion of the support member and the hollow shaft of the dose setting member. Preferably, the hollow shaft as well as the socket portion comprise a circular geometry. The last dose limiting member is in particular sandwiched between the socket portion and the hollow shaft.

The last dose limiting member is furthermore engaged with the socket portion and with the hollow shaft in such a way, that a rotation of the hollow shaft, hence of the dose setting member relative to the socket portion leads to a displacement of the dose limiting member along the socket portion, hence radially inwardly or radially outwardly with respect to the overall geometry of the housing. In this context a radially directed displacement corresponds to a displacement along the longitudinal axis of the socket portion.

In particular, the last dose limiting member may be threadedly engaged with the socket portion and may be rotatably fixed and slidably displaceable relative to the hollow shaft. This way, a rotation of the hollow shaft relative to the socket portion slaves the dose limiting member around the socket portion, thereby following an outer thread of the socket portion. In this embodiment the last dose limiting member comprises a correspondingly shaped threaded portion to mate with the outer thread of the socket portion.

In an alternative embodiment, the last dose limiting member is threadedly engaged with a hollow shaft and is rotatably fixed and slidably displaceable to the socket portion. Here, an inside facing side wall of the hollow shaft is threadedly engaged with the dose limiting member while the dose limiting member is splined to the socket portion. Then, a rotation of the hollow shaft and hence of the dose setting member relative to the socket portion leads to a radially directed displacement of the dose limiting member relative to the socket portion.

Since a rotation of the dose setting member relative to the support member or relative to the housing is only allowed and possible in the dose setting mode, the last dose limiting member will be displaced relative to the hollow shaft only during dose setting or dose correcting procedures. During dose dispensing, the last dose limiting member will remain stationary since the dose setting member and hence its hollow shaft is rotatably locked and fixed by the locking member of the depressed dose injection member.

Naturally, the travel path the last dose limiting member is allowed to travel along the socket portion is adapted and correlated to the maximum distance the piston rod of the drive mechanism may advance in distal direction during consecutive dose dispensing procedures. Accordingly, the threaded engagement of the last dose limiting member and the socket portion of the support member as well as the elongation of the socket portion are designed and chosen accordingly in order to match with the size of the cartridge and the amount of medicament contained therein. Moreover, the position of the last dose limiting member relative to the socket portion of the support member is unequivocally correlated and always corresponds to the axial position of the piston rod and hence to the axial position of the piston of the cartridge operably engaged with the piston rod of the drive mechanism.

In a further preferred embodiment the last dose limiting member is displaceable along the socket portion only between a zero dose limiting stop and a last dose limiting stop. Preferably, the zero dose limiting stop as well as the last dose limiting stop radially extend from opposite end portions of the socket portion or from opposite end portions of the hollow shaft. Preferably, the zero dose limiting stop and the last dose limiting stop extend radially from the threaded socket portion or from the threaded hollow shaft of the dose limiting member, depending on how the mutual engagement of last dose limiting member, socket portion and hollow shaft is implemented.

The zero dose limiting stop as well as the last dose limiting stop typically extend radially outwardly at the end of an external threaded portion of the socket portion. In this way, a revolving motion of the last dose limiting member around the socket portion or around the hollow shaft can be blocked and delimited when the last dose limiting member gets in radial abutment with either the zero dose limiting stop or with the last dose limiting stop. Typically, after the device is assembled, the last dose limiting member disposed in abutment with the zero dose limiting stop. This way, a rotation of the dose setting member in a dose decrementing direction can be effectively blocked. Hence, in an initial device configuration, the dose setting member can only be dialed in a dose incrementing direction, thereby displacing the last dose limiting member away from the zero dose limiting stop.

In the event that the medicament in the cartridge is almost used up and when the piston of the cartridge almost reaches a distal end position, the last dose limiting member will be located proximate to the last dose limiting stop. In such a configuration, the dose setting member may be dialed in a dose incrementing direction until the last dose limiting member abuts with the last dose limiting stop. When the last dose limiting member engages with the last dose limiting stop, a further rotation of the hollow shaft and hence of the dose setting member is effectively blocked and setting of a dose exceeding the amount of medicament remaining in the cartridge can be effectively prevented.

Moreover, since the dose setting member is directly engaged with the last dose limiting member and since a rotation of the last dose limiting member relative to socket portion of the support member and hence the housing can be blocked by a last dose stop, a rather direct and robust feedback can be provided to a user of the device when the drive mechanism reaches the last dose limiting configuration.

By having the last dose sleeve in direct engagement with the dose setting member, a tolerance chain of a last dose limiting mechanism is fairly short and the negative influence of inevitable mechanical tolerances and mechanical play between various functional and mutually engaging components of the drive mechanism can be reduced to a minimum.

According to another embodiment, the drive sleeve is rotatably and axially slidably engaged with a dose indicating sleeve threadedly engaged with the inside of the housing. Preferably, the dose indicating sleeve at least partially houses the drive sleeve. In particular, in axial direction, the dose indicating sleeve is arranged at least in part around the outer circumference of the drive sleeve. The drive sleeve and the dose indicating sleeve may be splined so that a rotation of the drive sleeve is directly transferable to a corresponding rotation of the dose indicating sleeve.

The mutual engagement of the drive sleeve and the dose indicating sleeve further enables the dose indicating sleeve to slide along the drive sleeve in axial direction. Since the dose indicating sleeve is threadedly engaged with the inside of the housing, a rotation of the drive sleeve leads to a corresponding rotation of the dose indicating sleeve, which due to its threaded engagement with the housing becomes subject to a helical or screw-like motion. The outside of the dose indicating sleeve is provided with consecutive numbers indicating the amount of a dose actually set by the drive mechanism. Depending on the degree of rotation of the drive sleeve, a respective number of the dose indicating sleeve will show up in a dose indicating window of the housing.

Moreover, the dose indicating sleeve comprises at least one stop at one axial end to abut with a single dose limiting stop located on the inside of the housing. The single dose limiting stop of the housing typically extends in axial direction to allow and to support a circumferentially or tangentially acting mutual abutment of drive sleeve and housing when reaching a zero dose or a maximum dose configuration. Accordingly, the at least one stop provided at one axial end of the dose indicating sleeve extends in axial direction to get in direct circumferential or tangential abutment with the correspondingly shaped single dose limiting stop at the inside of the housing.

Irrespective on whether the drive mechanism is in dose dispensing or dose setting mode the dose indicating sleeve and the drive sleeve are rotatably fixed. Therefore, a revolving or turning motion of the drive sleeve, either for dose incrementing or dose decrementing equally transfers to a respective rotation of the dose indicating sleeve. Typically, the drive mechanism rotates in one direction, e.g. in clockwise direction during a dose setting procedure and rotates in the opposite direction, e.g. during dose injection. Accordingly, the numbers provided on the outside of the dose indicating sleeve and being visible through the dose indicating window of the housing, will count up and count down during dose setting and dose dispensing, respectively.

According to another embodiment, the drive sleeve is rotatably biased relative to the housing by means of a helical spring extending around the drive sleeve. The helical spring is coupled with one end with the drive sleeve while another end of the helical spring is preferably coupled and connected with the housing. This way, the drive sleeve is rotatably supported for setting of a dose relative to housing against the action of the helical spring.

Such rotational and spring biasing displacement of the drive sleeve is preferably accompanied and controlled by a ratchet mechanism of the drive sleeve having at least one ratchet member to engage with a toothed profile or toothed surface of the housing to prevent uncontrolled and counter-directed rotation of the drive sleeve. Typically, thee drive sleeve comprises a resiliently deformable arc-shaped ratchet member extending along the outer circumference of the drive sleeve and having a ratchet tooth or nose extending radially outwardly and mating with a correspondingly shaped toothed surface provided on the inner wall of the housing.

Alternatively, also the housing may be equipped with a radially resiliently deformable ratchet member to engage with a geared or toothed profile at the outer circumference of the drive sleeve.

This way, the drive sleeve may be stepwise rotated in a dose incrementing direction as governed by the size of the toothed surface. Moreover, a dose incrementing dialing or rotation of the drive sleeve is accompanied with an audible click-sound generated by the ratchet member meshing with the toothed profile.

Mutual engagement of the ratchet member of the drive sleeve with the toothed profile of the housing is further designed in such a way, that a user may also correct the size of a set dose, e.g. by rotating the drive sleeve in an opposite direction. However, for such a correcting and oppositely directed rotation of the drive sleeve, application of a counter-directed correction force is to be applied to the dose setting member, which is larger than a holding force provided by the mutual engaging ratchet member and the toothed surface.

Apart from application of a counter-directed correction force above a predefined force level, other dose-correcting mechanisms are also conceivable here by means of which the ratchet mechanism may be temporally overridden.

According to a further embodiment, the piston rod is threadedly engaged with a drive nut which is axially fixed to the housing and which is rotatably supported in the housing. Preferably, drive nut and drive sleeve are co-aligned around the piston rod. The drive nut may be located distally from a distal end of the drive sleeve and is preferably axially secured in the housing. The piston rod is typically splined to the housing or to an insert fixedly attached to and positioned in the housing and providing a radially inwardly extending flange or web with a through opening, through which the piston rod may extent axially.

Moreover, the drive sleeve is rotatably engaged with the drive nut when in dose injecting position and the drive sleeve and drive nut are disengaged when the drive sleeve is in its dose setting position.

It is to be mentioned here, that the insert is fixed and immobilized to the housing. The insert may be provided as a separate component to be assembled in the housing. Alternatively, insert and housing may be integrally formed. Hence, any reference made herein to the housing is equivalently valid for the housing and vice versa.

The through opening of the flange or web of the housing or of the respective insert comprises at least one radially inwardly extending protrusion that mates and engages with the at least one axially elongated groove of the piston rod. Consequently, the piston rod is rotatably fixed to the housing and is effectively hindered to rotate relative to the housing. A distally directed displacement of the piston rod relative to the housing can thus be attained by the rotating drive sleeve threadedly engaged with the piston rod.

The drive nut is preferably only free to rotate in one direction relative to the housing that corresponds to a dose setting procedure, during which the piston rod is driven in distal direction. Hence, the drive nut may be equipped with another ratchet mechanism operating in an opposite sense compared to the ratchet mechanism of the drive sleeve. The drive nut's ratchet mechanism only allows a dispensing-correlated rotation of the drive nut relative to the housing but prevents a counter-directed rotation. In a similar way, also the ratchet mechanism of the drive nut may comprise e.g. an arc-shaped ratchet member extending in tangential or circumferential direction at the outer circumference of the drive nut.

Also here, the ratchet member may comprise a ratchet tooth to resiliently engage with a correspondingly shaped toothed surface at an inside facing portion of the sidewall of the housing or of a corresponding insert.

Alternatively, the housing or insert may be equipped with a radially resiliently deformable ratchet member to engage with a geared or toothed profile at the outer circumference of the drive nut.

For dispensing of a set dose, it is intended that the drive sleeve is axially displaceable relative to the housing for rotatably engaging the drive sleeve and the drive nut. Here, a distal end or a distal face of the drive sleeve is adapted to rotatably engage with an opposite and hence proximal face of the drive nut. Drive nut and drive sleeve therefore comprise mutually corresponding and axially extending positive locking means, such like crown wheels in order to transfer angular momentum from the drive sleeve to the drive nut during a dose dispensing procedure.

Typically, the drive sleeve is biased in axial direction relative to the housing by means of one or several spring elements. If the drive sleeve after completion of a dose setting procedure is displaced against respective spring forces in distal direction, it may first rotatably engage with the drive nut and it may then consecutively rotatably disengage from the housing. The distally directed displacement of the drive sleeve may therefore disengage the ratchet mechanism by way of which the drive sleeve is rotatably locked to the housing. Once such a release configuration is obtained, the drive sleeve is free to rotate relative to the housing under the effect of the relaxing helical spring.

Since in this release configuration the drive sleeve is operably and rotatably engaged with the drive nut, the drive nut may rotate accordingly, thereby advancing the piston rod in distal direction. It is to be noted that the drive nut's ratchet mechanism operates in the opposite sense compared to the ratchet mechanism of the drive sleeve. Also here, rotation of the drive nut during dose dispensing may be accompanied by consecutive click-sounds generated by its ratchet member meshing with a correspondingly shaped toothed profile.

According to another aspect, the invention also relates to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

Apart from that, the drug delivery device and the drive mechanism may comprise further functional components, such like a dose injection member, by way of which a user may trigger and control the drug delivery device and its drive mechanism for dispensing of a dose of the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

While the axial direction typically coincides with the longitudinal direction or longitudinal elongation of the housing, the radial direction coincides with a lateral or transverse direction typically extending perpendicular to the axial or longitudinal direction. The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a brief description of the drawings is provided, in which:

FIG. 4 shows a cross-section along A-A according to FIG. 2, FIG. 5 shows a cross-section along B-B according to FIG. 2, FIG. 6 shows a cross-section through the device along C-C according to FIG. 2, FIG. 7 shows a cross-section along D-D according to FIG. 2, FIG. 8 is indicative of a cross-section along E-E according to FIG. 2 and FIG. 9 shows a cross-section along F-F according to FIG. 2, FIG. 10 perspectively shows an enlarged view of the gear wheel of the dose setting member engaged with the crown wheel of the drive sleeve.

DETAILED DESCRIPTION

Figure 1:
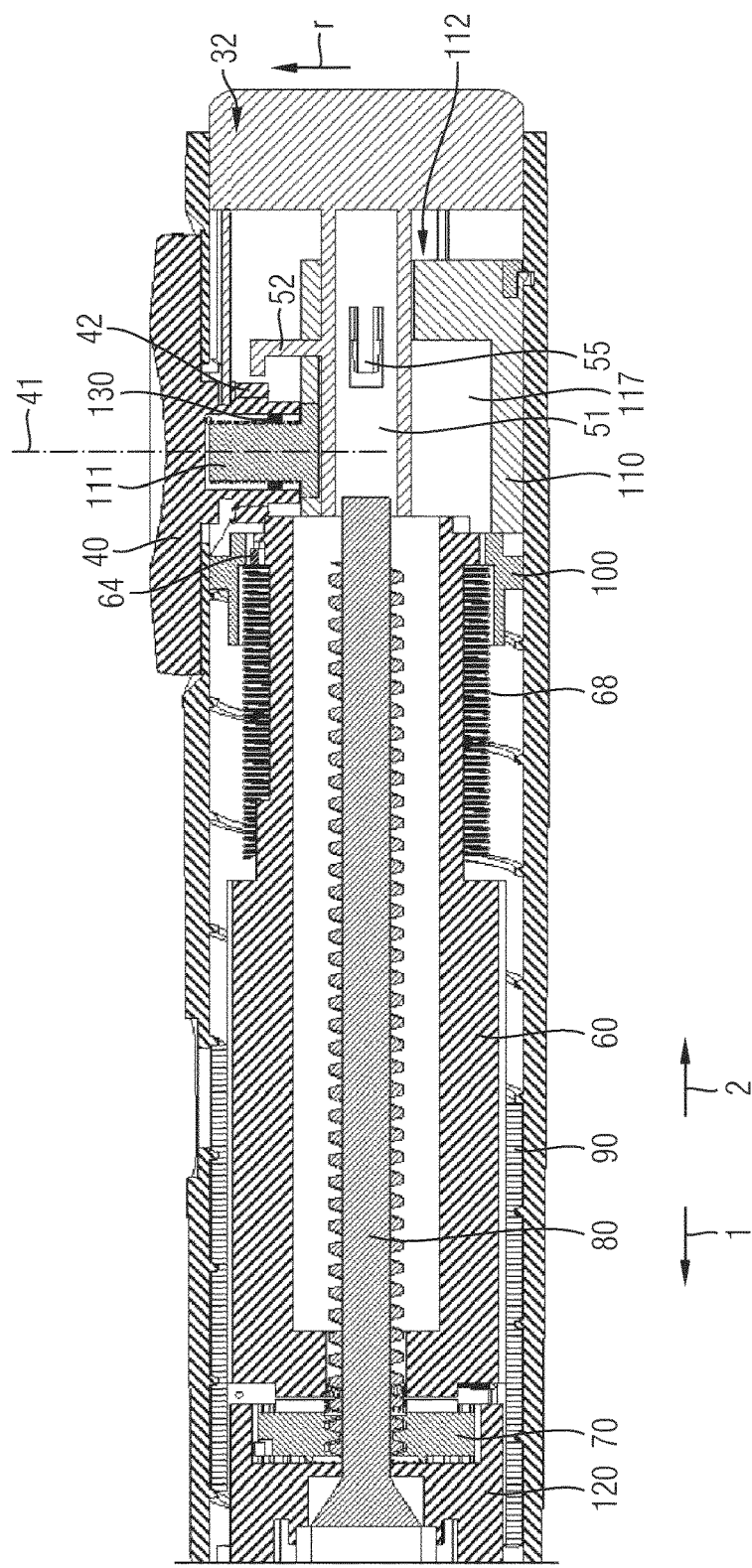
FIG. 1 schematically illustrates the assembled drive mechanism in a longitudinal cut, FIG. 2 schematically illustrates the entire drug delivery device in a longitudinal cut, FIG. 3 perspectively illustrates an exploded view of the entire drug delivery device.

In FIG. 3, the drug delivery device 10 is illustrated in an exploded view. The drug delivery device 10 of pen-injector type comprises a substantially cylindrical and axially elongated shape. Throughout the Figures, the axial distal direction is denoted with reference number 1 and the opposite proximal direction is denoted with reference number 2. The drug delivery device 10 which is also shown in an assembled configuration in FIG. 2 in longitudinal cross section comprises a drive mechanism 3 arranged in a proximal housing 30.

In distal direction, the housing 30 is connected with a cartridge holder 12 which is adapted to accommodate and to receive a cartridge 14 containing the medicament to be dispensed by the drug delivery device 10. The cartridge 14 typically comprises a vitreous barrel 18 of cylindrical shape which is sealed in distal direction 1 by a pierceable sealing member, such like a septum.

In proximal direction 2, the cartridge 14 is sealed by a piston 16 slidably arranged in the vitreous barrel 18 of the cartridge 14. Displacement of the piston 16 in distal direction 1 leads to a respective built-up of a fluid pressure inside the cartridge 14. When the distal outlet of a cartridge 14 is connected with e.g. a needle assembly 20, as for instance indicated in FIG. 2, a predefined amount of the liquid medicament contained in the cartridge 14 can be expelled and dispensed via an injection needle 22 of the needle assembly 20.

Figure 2:
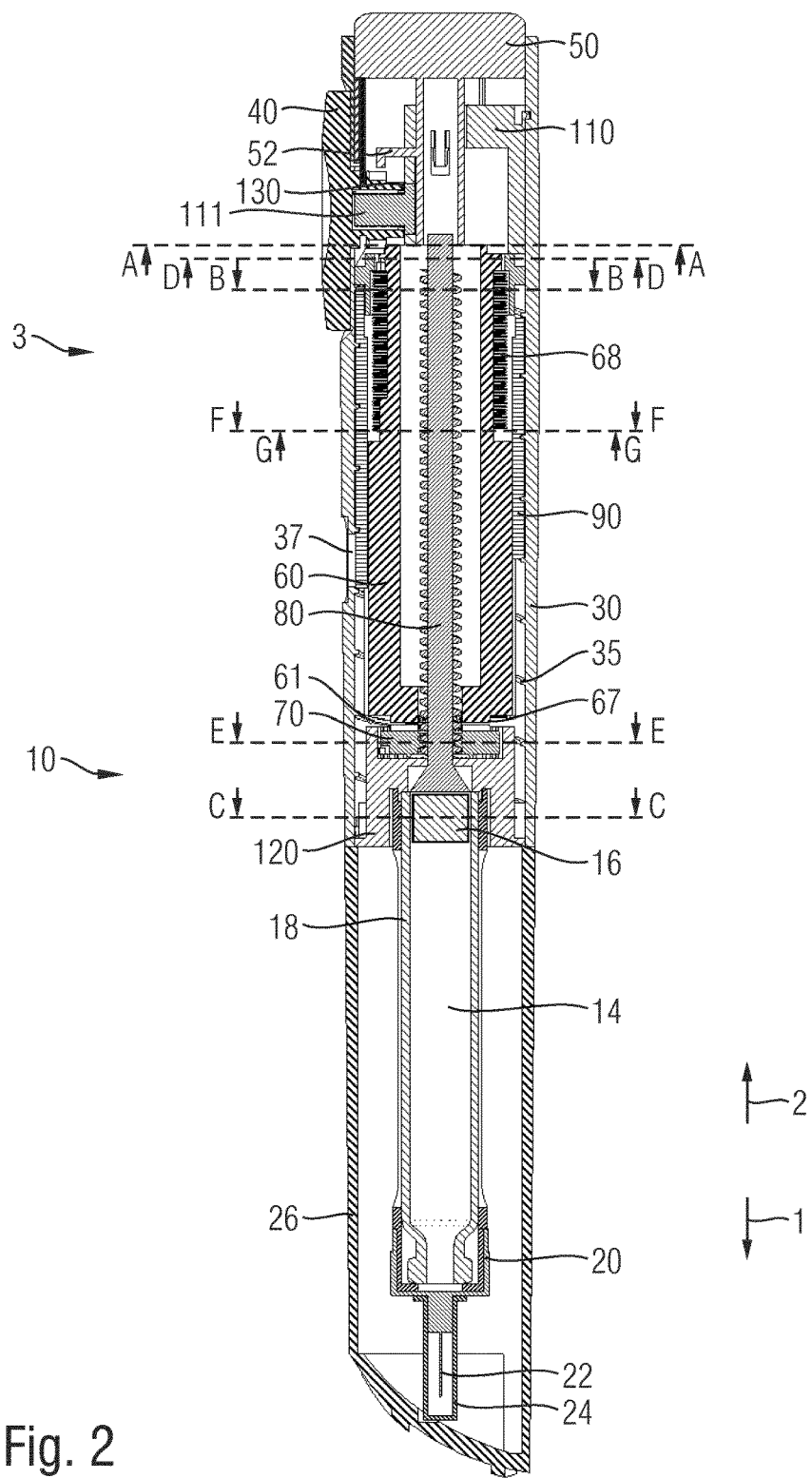

In FIG. 2 however, an inner needle cap 24 to protect the double-tipped injection needle 22 is indicated. The needle assembly 20 is typically arranged on a distal end portion of the cartridge holder 12. Typically, a distally located socket of the cartridge holder 12 and the needle assembly 20 comprise mutually corresponding threads to screw the needle assembly 20 onto the cartridge holder 12 in a releasable and removable way.

The cartridge holder 12 and hence the cartridge 14 is to be protected and covered by a protective cap 26 which is shown in FIGS. 2 and 3. Prior to setting and/or dispensing of a dose, the protective cap 26 as well as the inner needle cap 24 are to be removed. After dispensing or injecting of the medicament into biological tissue, the needle assembly 20 is typically to be discarded and the distal end of the drug delivery device 10 is to be covered by the protective cap 26.

The drive mechanism 3 as illustrated in an exploded view in FIG. 3 and as shown in cross section in its fully assembled configuration in FIGS. 1 and 2 comprises numerous functional components by way of which a dose of variable size can be set and subsequently dispensed.

The dose dispensing procedure comes along with a distally directed advancing displacement of the piston rod 80 relative to the housing 30. The drive mechanism 3 therefore comprises at least a housing 30, a piston rod 80 and a drive sleeve 60 which can be released and operably engaged with the piston rod 80 for selectively setting and dispensing of a dose.

It is to be noted here, the embodiments as illustrated in FIGS. 1 to 25 are only exemplary for one of a plurality of conceivable drive mechanisms that may be equipped with the single dose limiting mechanism as well as the last dose limiting mechanism according to the present invention.

In the following setting of a dose is described.

For setting of a dose, a user grips the drug delivery device 10 and starts to rotate the actuation wheel 44 of the dose setting member 40 in a clockwise or counter clockwise direction for incrementing a dose to be set and to be subsequently dispensed by the drug delivery device 10. As illustrated in FIGS. 1, 4, 19 and 20 the dose setting member 40 comprises a radially inwardly extending shaft portion 43 receiving a radially outwardly extending socket portion 111 of a support member 110 fixedly attached in a proximal portion of the housing 30.

The shaft 43 is integrally formed with the dose setting member 40 and comprises an actuation wheel 44 at its outer circumference. The actuation wheel 44 extends outside of a sidewall portion 31 of the housing 30. In particular, the actuation wheel 44 may comprise a diameter extending the radial diameter of the tubular housing 30. As shown FIG. 4, the housing 30 may provide a lateral and substantially even shaped plateau to support actuation wheel 44. As further illustrated in FIG. 1, the dose setting member 44 is rotatable with respect to an axis of rotation 41 extending in radial direction (r).

Figure 10:
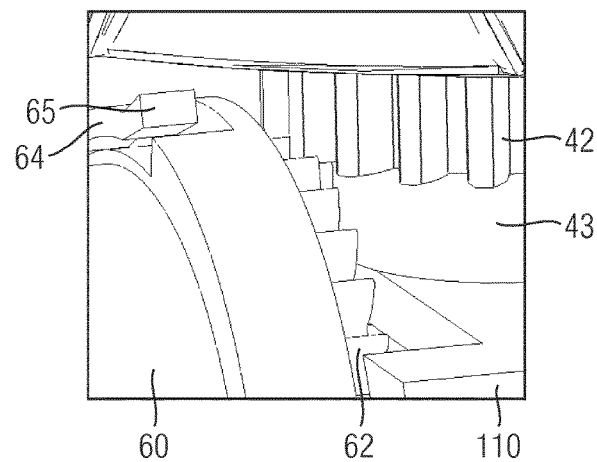
Figure 11:
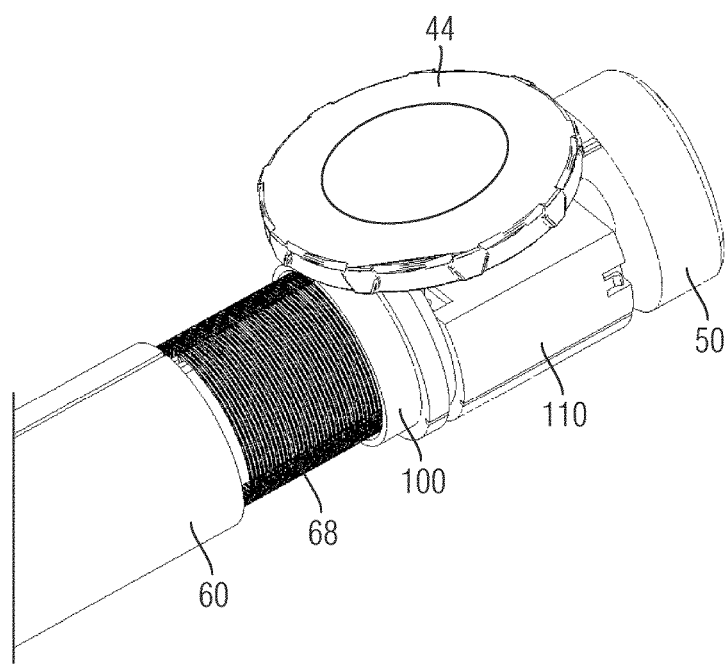
FIG. 11 is illustrative of a perspective view of assembled components of the drive mechanism without the circumferential housing.
Figure 12:
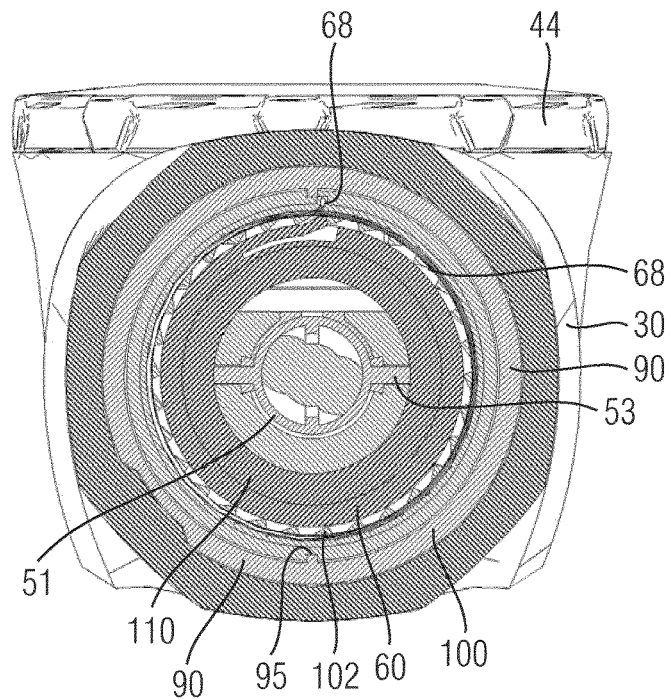
FIG. 12 shows a cross-section G-G through the device according to FIG. 2.
Figure 13:
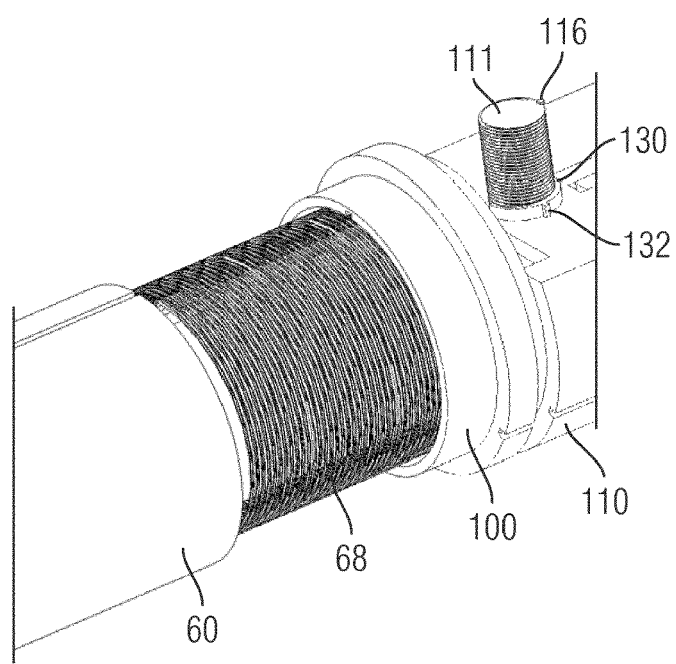
FIG. 13 is illustrative of another perspective view of assembled components of the drug delivery device.
Figure 14:
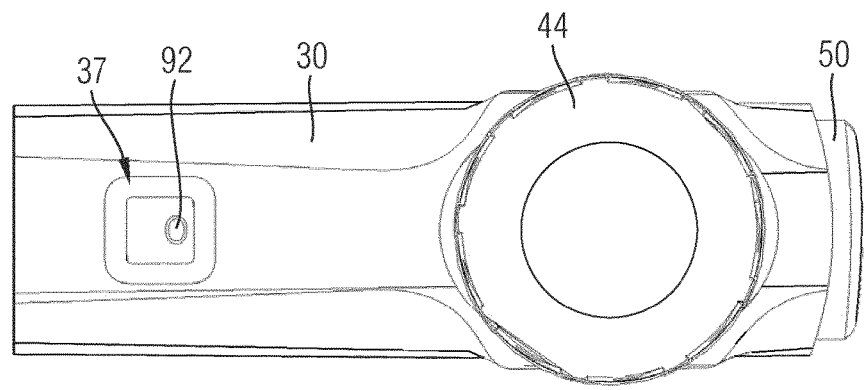
FIG. 14 is a perspective view of the proximal housing of the drug delivery device.
Figure 15:
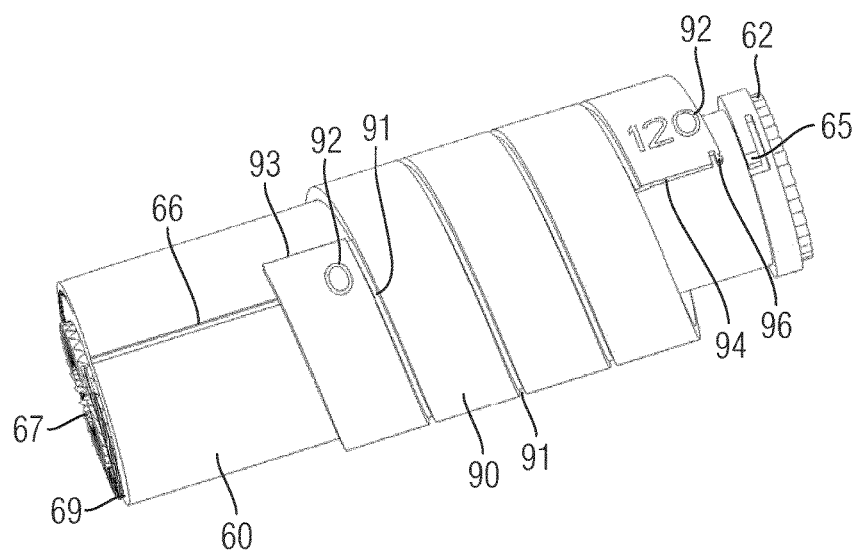
FIG. 15 is a perspective view of a nested arrangement of drive sleeve and dose indicating sleeve.
Figure 16:
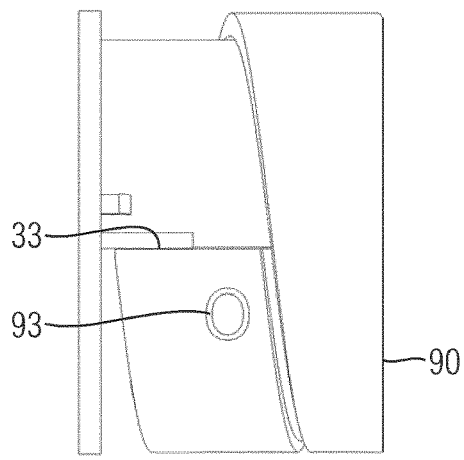
FIG. 16 shows the dose indicating sleeve in a distal abutment with the housing, FIG. 17 perspectively illustrates mutual abutment of the dose indicating sleeve and the housing in a proximal abutment configuration.

As indicated in the enlarged view of FIG. 10, an inner gear wheel 42 or the outwardly extending toothed surface of the shaft 43 of the dose setting member 40 is engaged with a crown wheel 62 located on a proximal end face of the drive sleeve 60 which is also shown in FIG. 15. Hence, a rotation of the dose setting member around the radially extending axis 41 leads to a corresponding rotation or revolving of the drive sleeve 60 around a longitudinal axis, which may coincide with the piston rod 80 located in a central portion of the drive sleeve 60.

Figure 19:
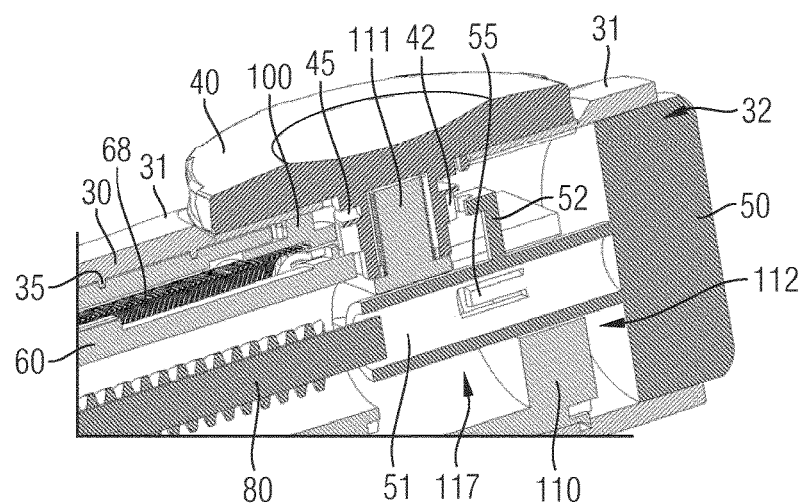
FIG. 19 shows a partially cut and perspective view of assembled components of the drive mechanism.

The drive sleeve 60 is operably engaged with a helical spring 68 arranged around a proximal portion of the drive sleeve 60 as indicated in cross-section according to FIG. 1 and FIG. 19. A distal end of the helical spring 68 is connected with the drive sleeve 60. As shown in cross-section in FIG. 9, the drive sleeve 60 comprises a radially outwardly extending notch 63 to engage with a free end of the helical spring 68. An opposite end, hence a proximal end of the helical spring 68 is attached to a locking member 100 located around a distal end portion of the drive sleeve 60.

As indicated in FIG. 5 the locking member 100 comprises a radially outwardly extending notch 101 at its inside facing side wall portion to receive the proximal free end of the helical spring 68. The locking member 100 is fixedly attached in the housing 30. Therefore, a dose incrementing rotation of the dose setting member 40 leads to a corresponding rotation of the drive sleeve 60 against the restoring force of the helical spring 68 arranged between the drive sleeve 60 and the locking member 100.

Even though the locking member 100 is provided as a separate component it serves as a component of the housing 30 since it is fixedly attached thereto. Hence, any reference to the locking member 100 made herein equally applies to the housing 30 and vice versa. Alternatively, the locking member 100 could also be integrally formed with the housing 30. It is predominately due to the assembly and manufacturing process that the locking member 100 is provided as a separate part to be assembled and fixedly attached in the housing 30.

As indicated in FIG. 15 and as shown in cross-section in FIG. 7, the drive sleeve 60 further comprises an arc-shaped ratchet member 64 near a proximal end thereof. The ratchet member 64 is resiliently deformable in radial direction and comprises a radially outwardly extending tooth or nose 65 mating with a correspondingly shaped toothed profile 102 of the locking member 100 arranged around the circumference of the drive sleeve's ratchet member 64.

As indicated in the cross-section D-D of FIG. 7, the tooth 65 provided at a free end of the resiliently deformable ratchet member 64 meshes with the toothed profile 102 of the locking member 100 when rotating counter clockwise relative to the locking member 100, hence during a dose incrementing rotation of the drive sleeve 60. Here, passing of the tooth 65 along the toothed profile 102 generates an audible feedback to the user, thereby indicating, that the dose is step-wise incremented.

The geometry of the toothed surface 102 of the locking member 100 and the tooth 65 is designed such, that the spring force arising from the helical spring 68 and acting in opposite, hence clockwise direction on the drive sleeve 60 is not large enough to rotate the drive sleeve 60 in the opposite, hence clockwise sense. This way, mechanical energy can be stored by and in the helical spring 68 which is to be released only on demand during a subsequent dose dispensing procedure.

Even though not particularly illustrated here, the toothed surface 102 and the ratchet member 64 of the dose sleeve 60 engage in such a way, that a dose decrementing rotation of the drive sleeve 60 is indeed possible, e.g., when a user exerts a respective counter-directed angular momentum to the dose setting member 40, which exceeds the resilient resistance provided by the mutually engaged ratchet member 64 and the toothed surface 102.

Figure 17:
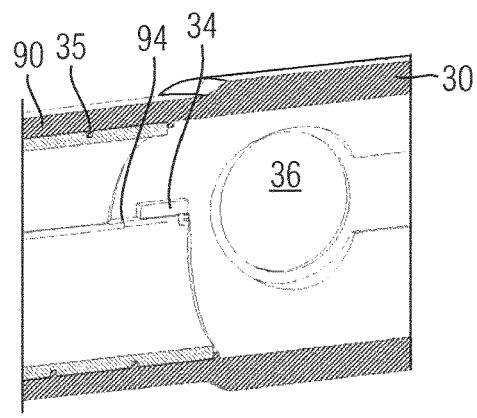

A dose incrementing action governed by a rotation of the dose setting member 40 and a corresponding rotation of the drive sleeve 60 also leads to a corresponding rotation of a dose indicating sleeve 90. The dose indicating sleeve 90 is comprises numerous dose indicating numbers 92 at its outer circumference arranged in a helical way, as for instance indicated in FIG. 15. Moreover, the dose indicating sleeve 90 comprises an outer thread 91 threadedly engaged with an inner thread 35 on the inside facing sidewall portion of the housing 30 as indicated in FIGS. 15 and 17.

A rotation of the drive sleeve 60 unalteredly and directly transfers to a respective rotation of the dose indicating sleeve 90 since the drive sleeve 60 comprises two diametrically oppositely disposed and longitudinally extending grooves 66 on its outer circumference that receive and engage with two correspondingly shaped, radially inwardly extending projections 95 of the dose indicating sleeve 90 as shown in FIG. 9. As illustrated there, the drive sleeve 60 is directly splined to the dose indicating sleeve 90.

The splined engagement of the drive sleeve 60 and the dose indicating sleeve 90 further allows for an at least limited sliding axial displacement between the dose indicating sleeve 90 and the drive sleeve 60, in particular during a mode switching of the drive mechanism 3.

When during a dose setting procedure the drive sleeve 60 is rotated relative to the housing 30 also the dose indicating sleeve 90 becomes subject to a respective revolving motion. Hence, the dose indicating sleeve 90 will always instantly show a corresponding dose size indicating number 92, representing e.g. an amount of international units (I.U.) of a medicament in a dose displaying window 37 of the housing 30. As indicated for instance in FIG. 14, the dose indicating window 37 may comprise a recess or a through opening in the sidewall of the housing 30.

Decrementing of the dose, hence dialing the dose setting member 40 and the drive sleeve 60 in an opposite sense of rotation, leads to a respective counter-rotation of the dose indicating sleeve 90. Consequently, decreasing dose indicating numbers will consecutively show up in the dose indicating window 37.

The dose indicating sleeve 90 not only serves to visually indicate the size of the dose actually set by a user of the device but also provides a single dose limiting arrangement when interacting with the surrounding housing 30.

As indicated in FIGS. 15-18 and due to the threaded engagement of the dose indicating sleeve 90 with the housing 30, the dose indicating sleeve 90 starts to fulfil a helically revolving, hence a screw-like motion relative to the housing 30 during dose setting. Additionally, the dose indicating sleeve 90 comprises a distal stop 93 at a distal end. The distal stop 93 comprises an axially extending edge at the outer circumference of the dose indicating sleeve 90. Corresponding to its distal end the dose indicating sleeve 90 also comprises a proximal stop 94 in the form of an axially extending edge at a respective proximal end.

When the drive sleeve 60 is rotated in a dose incrementing direction, the dose indicating sleeve 90 will advance in distal direction 1 until the leading edge of the distal stop 93 abuts with an axially and radially extending distal stop 33 of the housing 30. In this situation a maximum dose size has been set and a further dose incrementing dialing of drive sleeve 60 is blocked. Typically, a maximum dose number 92 will then show up in the dose indicating window 37 of the housing 30. In the illustrated embodiment of FIG. 6 and FIG. 16, the distal stop 33 actually protrudes radially outwardly from an insert 120 fixedly arranged in the housing 30. However, the insert 120 may also be integrally formed with the housing 30 so that any reference made herein to the housing 30 equally applies to the insert 120, and vice-versa. Alternatively, the distal stop 33 may also protrude radially inwardly from the housing 30.

The radially extending distal stops 33, 93 of insert 120 or housing 30 and the dose indicating sleeve 90 provide a well-fined dose limiting configuration and effectively block a further dose incrementing movement of the dose indicating sleeve 90 and hence of the drive sleeve 60 rotatably coupled therewith.

In the opposite direction the housing 30 comprises a proximal stop 34 extending also in axial and radial direction. The proximal stop 34 of the housing 30 is adapted to correspondingly engage and to abut with the proximal stop 94 of the dose indicating sleeve 90 when a zero dose configuration has been reached. A respective abutment configuration is shown in FIG. 17 and in FIG. 5.

Figure 18:
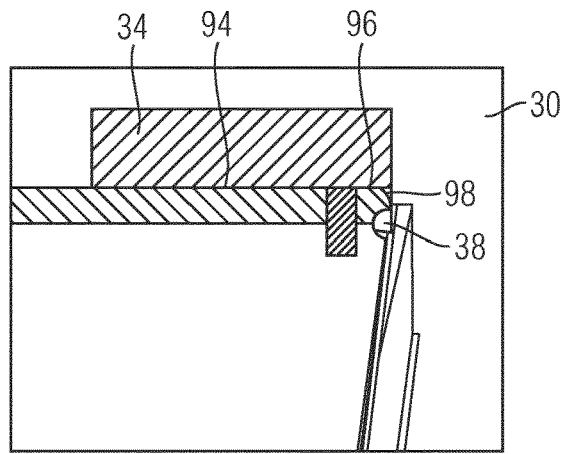
FIG. 18 shows an enlarged view of the mutual abutment of dose indicating sleeve and housing with a clicking member.

Additionally, the dose indicating sleeve 90 may comprise a clicking member 96 at its proximal and/or distal end. As indicated in FIG. 18, the clicking member 96 comprises a resiliently deformable latch or nose portion featuring a tilted edge 98 which is adapted to engage with an axially extending protrusion 38 provided at an inside facing sidewall section of the housing 30. The protrusion 38 is located tangentially or circumferentially offset from a proximal stop 34 so that the resiliently deformable clicking member 96 is resiliently deformed and biased immediately before the dose indicating sleeve 90 reaches a proximal or distal abutment configuration with the housing 30.

Shortly before or when the proximal or distal stop 94, 93 of the dose indicating sleeve 90 engages with the corresponding proximal or distal stop 34, 33 of the housing 30 or of the insert 120, the biased and resiliently deformed clicking member 96 returns into its rather unbiased configuration as illustrated in FIG. 18, thereby generating an audible click sound. This way, it is audibly indicated to a user, that either a maximum dose has just been set or that a minimum dose has just been set, which coincides also with a termination of a dose injection procedure. During dose injection, the dose sleeve 60 together with the dose indicating sleeve 90 will rotate in the opposite direction and will return to the zero dose configuration. Since returning into the zero dose configuration is accompanied with the audible click sound, the user is acoustically informed about the end of a dose injecting procedure.

In the following dispensing or injecting of a dose is described.

Once a dose has been correctly set, the drive mechanism 3 may be switched into a dispensing mode by depressing a dose injection member 50, located at a proximal end of the housing 30, in distal direction 1. The dose injection member 50 is slidably disposed in axial direction in a proximal receptacle 32 of the housing 30. The distal end of the axially extending shaft portion 51 of the dose injection member 50 is in direct abutment with a proximal end face of the drive sleeve 60. Preferably, the dose injection member 50 comprises at least two diametrically oppositely and radially outwardly extending abutment pieces 53 to axially engage with a proximal end face of the drive sleeve 60 as indicated in FIG. 4. Hence, distally directed displacement of the dose injection member 50 urges the drive sleeve 60 in distal direction 1 accordingly.

The dose injection member 50 also comprises a locking member 52 extending radially outwardly from the shaft portion 51 at a predefined axial distance from the gear wheel 42 of the dose setting member 40. However, by distally displacing the dose injection member 50 together with its rigidly connected locking member 52, the locking member 52 engages with the gear wheel 42 of the dose setting member 40 and thus inhibits a further rotation of the dose setting member 40. Therefore, a rotational interlock can be provided by the dose injection member 50 since the radially and axially extending locking member 52 extends through a longitudinal slit (not shown) of a support member 110 in which the dose injection member 50 is axially slidably supported.

Since the support member 110 is fixedly engaged in the housing 30 and since the dose injection member 50 is rotatably fixed to the support member 110, a rotation of the dose setting member 40 with respect to the housing 30 can be effectively blocked as soon as the toothed locking member 52 of the dose injection member 50 engages with the gear wheel 42 of the dose setting member 40.

Figure 25:
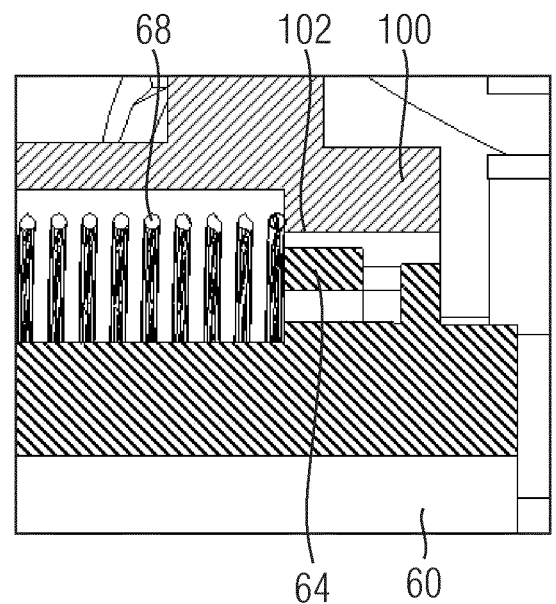
FIG. 25 shows an enlarged view of the drive sleeve disengaged from a ratchet member in the dose dispensing mode.

Hence, when in dose dispensing mode a further rotation of the dose setting member 40 is effectively blocked. By displacing the drive sleeve 60 from its proximal dose setting position into its distal dose injecting position, its ratchet member 64 gets released from the toothed profile 102 of the locking member 100 as shown in FIG. 25. Hence, the drive sleeve 60 is then free to rotate or to revolve around the piston rod 80 under the effect of the tension or biased helical spring 68.

Figure 24:
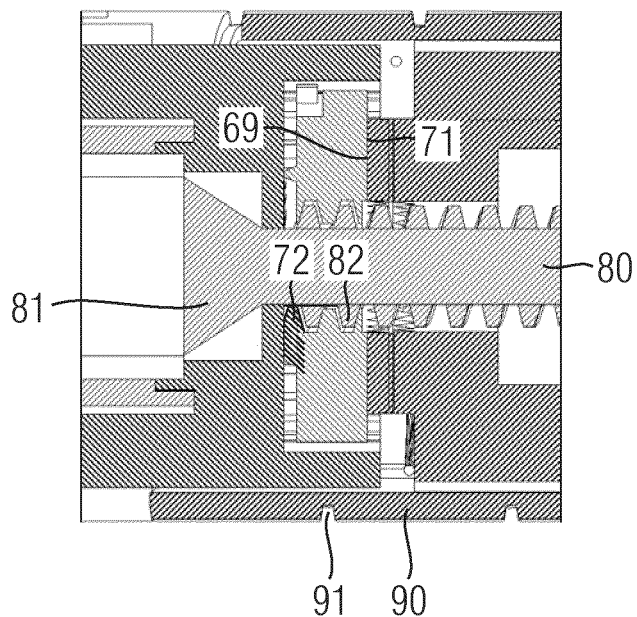
FIG. 24 shows a longitudinal cross-section through mutually engaging drive sleeve and drive nut.

The distally directed displacement of the drive sleeve 60 is limited by a drive nut 70 as illustrated in cross section in FIGS. 1 and 24. When in mutual axial abutment, the drive sleeve 60 and the drive nut 70 are rotatably engaged while the drive sleeve 60 and its ratchet member 64 is disengaged from the tooted profile 102 of the locking member 100. Mutual rotatable engagement of drive sleeve 60 and drive nut 70 is achieved by mutually corresponding teeth 67 or complementary interlocking members provided on a distal face 69 of the drive sleeve 60 and on a proximal face 71 of the drive nut 70, respectively. The proximal face 71 of the drive nut 70 may comprise crown wheels that correspond with correspondingly shaped crown wheels 67 provided on the distal face 69 of the drive sleeve 60.

Preferably, the axial extension of mutually corresponding crown wheels 67 located on the proximal face 71 and on the distal face 69 is such, that a rotational engagement of drive sleeve 60 and drive nut 70 is achieved before the ratchet member 64 of the drive sleeve 60 is released from the toothed profile 102 of the locking member 100 during a distally directed displacement of the drive sleeve 60. In this way, a substantially slipless coupling of drive sleeve 60 and drive nut 70 can be achieved.

Furthermore, by means of the distally directed displacement of the drive sleeve 60 relative to the housing 30 the proximally located crown wheels 62 of the drive sleeve 60 are released from the gear wheel 42 of the dose setting member 40. On the one hand, the distally directed displacement of the dose injection member 50 rotatably locks the dose setting member 40 relative to the housing 30 and on the other hand the dose injection member serves to simultaneously release the drive sleeve 60 from the operable engagement with the dose setting member 40.

The drive nut 70 is preferably axially fixed in an insert 120 fixedly attached in a distal portion of the housing 30. Even though not explicitly illustrated the insert 120 may comprise a circumferential or punctual recess to receive an axially acting fastening member for the drive nut 70 in order to fix the drive nut in axial direction.

The insert 120 further comprises two diametrically oppositely arranged and radially inwardly extending protrusions 121 that engage with a correspondingly shaped axially extending groove 84 of the piston rod 80. The piston rod 80 extends through the insert 120 in axial direction and comprises a pressure foot 81 at its distal end to directly engage with the piston 16 of the cartridge 14. Here, the piston rod 80 is rotatably fixed to the housing 30 or to the insert 120, by the radially inwardly extending protrusions 121 engaging with the longitudinal groove 84 of the piston rod 80. The radially inwardly extending protrusions 121 of the insert 120 may further be part of a web or flange portion featuring a through opening, through which the piston rod 80 extends axially.

The piston rod 80 comprises an outer thread 82 which is only threadedly engaged with an inner thread 72 of the drive nut 70.

When rotatably coupled, the drive sleeve 60 under the action of the biased helical spring 68 transfers an angular momentum to the drive nut 70, which in turn rotates around the radially fixed piston rod 80. The rotation of the axially fixed drive nut 70 then serves to advance the piston rod 80 in distal direction 1 for expelling of a dose of the medicament.

The drive nut 70 also comprises a ratchet member 74 having a circumferentially extending arm resiliently deformable in radial direction. At the free end of the ratchet member 74 a radially outwardly extending tooth 75 is located which is adapted to mesh with a correspondingly shaped toothed profile 122 provided at the inside facing wall of the insert 120. As indicated in cross section in FIG. 8 the ratchet member 74 and the toothed profile 122 are configured such, that only a clockwise, hence a dose dispensing rotation of the drive nut 70 is allowed while a counter-directed rotation of the drive nut 70 is effectively inhibited. This way, the piston rod 80 is only displaceable in distal direction 1 but not in proximal direction with respect to the housing 30 and/or with respect to the insert 120. The ratchet member 74 of the drive nut 70 and the toothed profile 122 of the insert 120 provide an effective anti-backup feature.

Moreover, during dose dispensing, when the drive nut 70 rotates in a dose decrementing direction the ratchet member 74 successively engages with consecutive teeth of the toothed profile 122 thereby generating an audible sound, e.g. a regular clicking indicating to a user that the injection is still in progress.

Distally directed displacement of the dose injection member 50 and the drive sleeve 60 may occur against the action of a spring 61, which is vaguely indicated in the cross-section according to FIG. 2. By means of the axially and distally extending spring 61, which may be integrally formed with the drive sleeve 60, the drive sleeve 60 is biased in axial direction against the insert 120 and/or against the housing 30.

Hence, distally directed displacement of the drive sleeve 60 occurs against the action of the integrated spring 61. An early or premature release of the dose injection member 50 prior to a termination of a dose dispensing procedure will then lead to an immediate proximally directed displacement of the drive sleeve 60 relative to the housing 30 under the effect of the integrated spring element 61. Consequently, the drive sleeve 60 will re-engage with the gear wheel 42 of the dose setting member 40 and will also re-engage with the toothed profile 102 of the locking member 100 for saving the mechanical energy stored in the biased helical spring 68.

Since a proximal end face of the drive sleeve 60 is in direct abutment with a distal portion, in particular with the two abutment pieces 53 of the dose injection member 50, the proximally directed returning displacement of the drive sleeve 60 will accordingly displace the dose injection member 50 into its proximal dose setting position.

Figure 20:
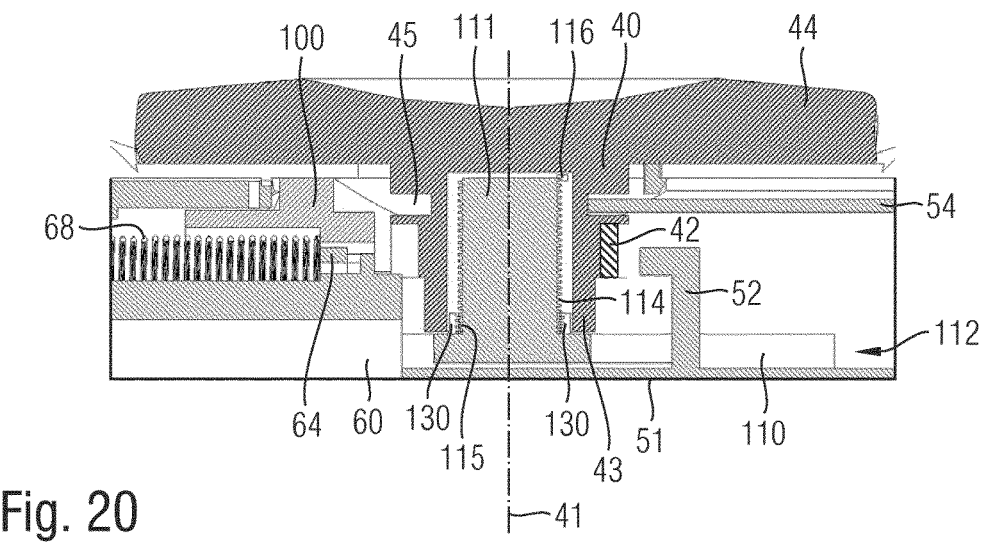
FIG. 20 shows a longitudinal cut through the arrangement according to FIG. 19.
Figure 21:
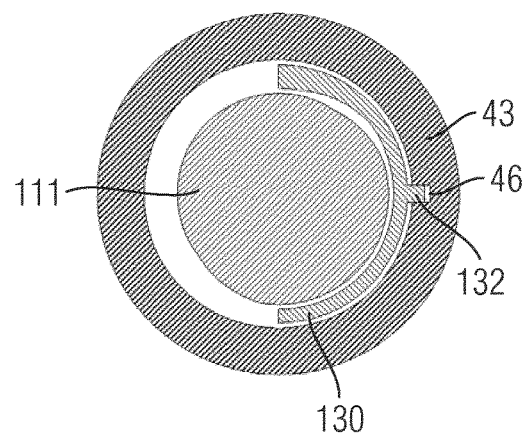
FIG. 21 shows a cross-section through a socket portion of the support member.
Figure 22:
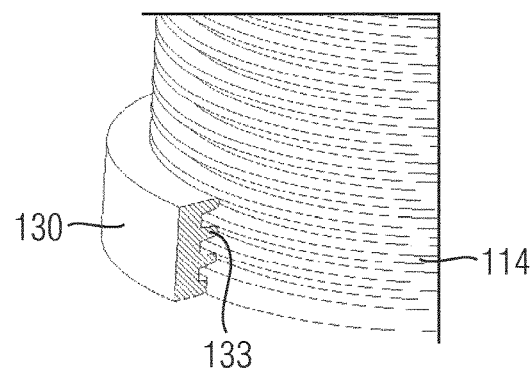
FIG. 22 is an enlarged view of the threaded engagement of the last dose limiting member and the socket portion.
Figure 23:
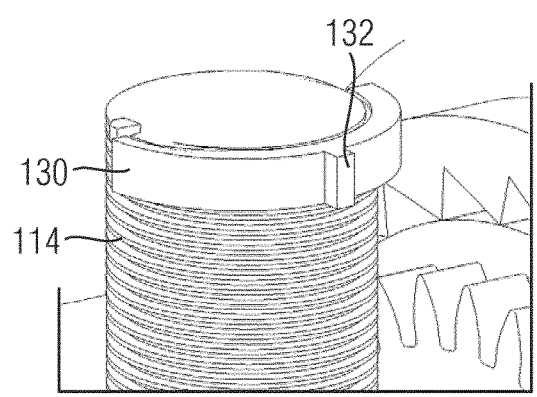
FIG. 23 shows the last dose limiting member in abutment with a last dose limiting stop at a free end of the socket portion.

For providing a last dose or end-of-content mechanism, a last dose member 130 is arranged between a radially outwardly extending socket portion 111 of the support member 110 and the hollow shaft 43 of the dose setting member 40. As in particular indicated in FIGS. 20-23, the last dose limiting member 130 is of arc shape and is threadedly engaged with the socket portion 111. Furthermore, as shown in FIGS. 21 and 23, the circular-shaped last dose limiting member 130 comprises a radially outwardly extending protrusion 132 engaging with a correspondingly shaped notch 46 extending at the inside of the shaft 43 of the dose setting member 40.

This way, the last dose limiting member 130 is rotatably fixed to the shaft 43 and to the dose setting member 40 but is actually threadedly engaged with the socket portion 111 of the support member 110. As shown in detail in FIG. 22, the last dose member 130 comprises an inner thread 133 threadedly engaged with the outer thread 114 of the socket portion 111 of the support member 110.

Due to the mutual engagement between the last dose member 130, the socket portion 111 and the shaft 43, the last dose limiting member 130 is allowed to slide along the shaft 43 and to rotate or to revolve around the socket portion 111 when the dose setting member 40 is rotated either in dose incrementing or dose decrementing direction. As for instance indicated in FIG. 20 and in FIG. 23, there is provided a zero dose stop 115 at a lower or inward facing end of the socket portion 111 and a last dose limiting stop 116 at an opposite, radially outwardly extending free end of the socket portion 111.

The zero dose stop 115 and the last dose limiting stop 116 both extend radially outwardly with respect to the elongation of the socket portion 111 in order to block or to inhibit a further rotation of the last dose limiting member 130 around the socket portion 111 as soon as a zero dose configuration or a last dose configuration has been reached.

Since the last dose limiting member 130 is rotatably coupled with the dose setting member 40, the position of the last dose limiting member 130 is indicative of accumulated and consecutive dose settings of the drive mechanism 3. During a dose dispensing procedure, the drive sleeve 60 will return into its initial configuration while the dose setting member 40 is hindered from rotating. This way and during consecutive dose setting procedures, the last dose limiting member 130 step-wise travels along the socket portion 111 towards the last dose limiting stop 116.

In effect, the position of the last dose limiting member 130 relative to the socket portion 111 and relative to the zero dose stop 150 and the last dose stop 116 is directly indicative of the axial position of the piston rod 80 and hence of the position of the piston 16 inside the cartridge 14. The last dose limiting member 130 may be active in both directions. Hence, in an initial configuration as illustrated in FIG. 20, which corresponds to an unused or completely filled cartridge, the last dose limiting member 130 effectively engages and radially abuts with the zero dose stop 150 thereby effectively preventing that a negative dose could be dialed or selected by a user. This way, in the initial configuration of the drive mechanism 3 dialing of a dose is only allowed in a dose incrementing direction.

As illustrated further in FIGS. 1 and 20, the dose injection member 50 further comprises an axially extending locking pin 54 extending into an annular-shaped groove 45 of the dose setting member 40. This way, the dose setting member 40 can be radially secured relative to the housing 30. Typically, the depth of the annular groove 45 is larger than the axial displacement of the dose injection member 50 between the proximal dose setting position and the distal dose injecting position. This way, the dose setting member 40 can be radially secured to the housing 30 irrespective on whether the drive mechanism 3 is in dose dispensing or dose setting mode. The dose setting member 40 also covers and extends into a through opening 36 of the housing 30 as indicated in FIG. 17.

As further illustrated in FIG. 19, the support member 110 comprises a centrally located and proximally directed receptacle 112 to receive the axially extending shaft portion 51 of the dose injection member 50. The receptacle 112 further comprises a radial recess 117 adapted to receive a radially outwardly extending latch element 55 integrated into the shaft portion 51. By means of the latch element 55, the dose injection member 50 can be axially secured in proximal direction relative to the support member 110 and hence relative to the housing 30.

LIST OF REFERENCE NUMERALS 1 distal direction
2 proximal direction
3 drive mechanism
10 drug delivery device
12 cartridge holder
14 cartridge
16 piston 18 barrel
20 needle assembly
22 needle
24 inner needle cap
26 protective cap
30 housing
31 side wall portion
32 receptacle
33 distal stop
34 proximal stop
35 thread
36 through opening
37 dose indicating window
38 protrusion
40 dose setting member
41 axis
42 gear wheel
43 shaft
44 actuation wheel
45 annular groove
46 notch
50 dose injection member
51 shaft portion
52 locking member
53 abutment piece
54 locking pin
55 latch element
60 drive sleeve
61 integrated spring
62 crown wheel
63 notch
64 ratchet member
65 tooth
66 groove
67 crown wheel
68 helical spring
69 distal face
70 drive nut
71 proximal face
72 inner thread
74 ratchet member
75 tooth
80 piston rod
81 pressure foot
82 outer thread
90 dose indicating sleeve
91 thread
92 number
93 distal stop
94 proximal stop
95 projection
96 clicking member
98 tilted edge
100 locking member
101 notch
102 toothed profile
110 support member
111 socket portion
112 receptacle
114 thread
115 zero dose stop
116 last dose stop
117 latch element
120 insert
121 protrusion
122 toothed profile
130 last dose limiting member
132 protrusion
133 inner thread

The invention claimed is:

1. A drive mechanism of a drug delivery device for dispensing of a dose of a medicament, the drive mechanism comprising:
   an elongated housing extending in an axial direction;
   a piston rod to operably engage with a piston of a cartridge to displace the piston in an axial distal direction;
   a drive sleeve extending in the axial direction and being rotatably supported in the elongated housing; and
   a dose setting member rotatably supported on a side wall portion of the elongated housing and being rotatable with respect to an axis extending in a radial direction relative to the axial direction, the dose setting member comprising a radially inwardly extending shaft relative to the elongated housing,
   wherein the drive sleeve is operably releasable from the piston rod and rotatably engageable with the dose setting member via the radially inwardly extending shaft for setting of the dose, and
   wherein the drive sleeve is displaceable in the axial direction between a proximal dose setting position and a distal dose injecting position for selectively and alternately engaging and disengaging with the piston rod and with the dose setting member.

2. The drive mechanism according to claim 1, wherein the drive sleeve is operably engageable with the piston rod and operably releasable from the dose setting member for dispensing of the dose.

3. The drive mechanism according to claim 1, further comprising a dose injection member at a proximal end of the elongated housing, wherein the dose injection member is displaceable in the axial direction between a proximal dose setting position and a distal dose injecting position and distally abuts with the drive sleeve for displacing the drive sleeve into the distal dose injecting position.

4. The drive mechanism according to claim 3, wherein the dose injection member is rotatably fixed to the elongated housing and comprises a locking member to engage with the dose setting member when reaching the distal dose injecting position.

5. The drive mechanism according to claim 3, wherein the drive sleeve is displaceable in the axial distal direction relative to the elongated housing against an action of a spring element axially acting between the drive sleeve and the elongated housing.

6. The drive mechanism according to claim 1, wherein the dose setting member comprises a gearwheel to engage with a crown wheel of the drive sleeve when in a dose setting position.

7. The drive mechanism according to claim 1 wherein the radially inwardly extending shaft is a hollow shaft and further comprising a support member fixedly attached to the elongated housing and having a radially outwardly extending socket portion to support the hollow shaft of the dose setting member.

8. The drive mechanism according to claim 7, wherein the support member further comprises an axially extending receptacle at a proximal end to slidably receive the dose injection member.

9. The drive mechanism according to claim 7, wherein a last dose limiting member is arranged between the socket portion and the hollow shaft, wherein the last dose limiting member is threadedly engaged with the socket portion and is rotatably fixed and slidably displaceable relative to the hollow shaft.

10. The drive mechanism according to claim 9, wherein the last dose limiting member is displaceable along the socket portion between a zero dose limiting stop and a last dose limiting stop radially extending from opposite end portions of the socket portion or the hollow shaft.

11. The drive mechanism according to claim 1, wherein the drive sleeve is rotatably and axially slidably engaged with a dose indicating sleeve threadedly engaged with an inside of the elongated housing, wherein the dose indicating sleeve comprises at least one stop at one axial end to abut with a single dose limiting stop located on the inside of the elongated housing.

12. The drive mechanism according to claim 1, wherein the drive sleeve is rotatably biased relative to the elongated housing by a helical spring extending around the drive sleeve.

13. The drive mechanism according to claim 1, wherein the piston rod is threadedly engaged with a drive nut axially fixed to the elongated housing and being rotatably supported in the elongated housing, wherein the drive sleeve is rotatably engaged with the drive nut when in a dose injecting position and wherein the drive sleeve and the drive nut are disengaged when the drive sleeve is in a dose setting position.

14. A drug delivery device for dispensing of a dose of a medicament, the drug delivery device comprising:
a drive mechanism comprising:
an elongated housing extending in an axial direction;
a piston rod to operably engage with a piston of a cartridge to displace the piston in an axial distal direction;
a drive sleeve extending in the axial direction and being rotatably supported in the elongated housing; and
a dose setting member rotatably supported on a side wall portion of the elongated housing and being rotatable with respect to an axis extending in a radial direction relative to the axial direction, the dose setting member comprising a radially inwardly extending shaft relative to the elongated housing,
wherein the drive sleeve is operably releasable from the piston rod and rotatably engageable with the dose setting member via the radially inwardly extending shaft for setting of the dose, and
wherein the drive sleeve is displaceable in the axial direction between a proximal dose setting position and a distal dose injecting position for selectively and alternately engaging and disengaging with the piston rod and with the dose setting member; and
the cartridge at least partially filled with the medicament and being arranged in the elongated housing of the drive mechanism or in a cartridge holder fixed to the elongated housing.

15. The drug delivery device according to claim 14, wherein the drive sleeve is operably engageable with the piston rod and operably releasable from the dose setting member for dispensing of the dose.

16. The drive mechanism according to claim 1, wherein the radially inwardly extending shaft extends radially inwardly into the elongated housing.

17. The drive mechanism according to claim 1, wherein the radially inwardly extending shaft comprises an outwardly extending toothed surface engageable with a crown wheel of the drive sleeve.

18. The drive mechanism according to claim 1, wherein the dose setting member comprises an actuation wheel located outside the side wall portion of the elongated housing.

19. The drive mechanism according to claim 18, wherein a diameter of the actuation wheel is larger than a diameter of the radially inwardly extending shaft.

\* \* \* \* \*